US009085641B2

(12) United States Patent
Schmetzer et al.

(10) Patent No.: US 9,085,641 B2
(45) Date of Patent: Jul. 21, 2015

(54) PEPTIDES REGULATING THE SURFACE EXPRESSION OF THE T CELL RECEPTOR

(75) Inventors: Oliver Schmetzer, Berlin (DE); Antonio Pezzutto, Berlin (DE)

(73) Assignee: Max-Delbruck-Centrum Fur Molekulare Medizin, Berlin (DE)

( * ) Notice: Subject to any disclaimer, the term of this patent is extended or adjusted under 35 U.S.C. 154(b) by 466 days.

(21) Appl. No.: 12/306,176

(22) PCT Filed: Jun. 23, 2007

(86) PCT No.: PCT/EP2007/005553
§ 371 (c)(1),
(2), (4) Date: Mar. 5, 2009

(87) PCT Pub. No.: WO2007/147630
PCT Pub. Date: Dec. 27, 2007

(65) Prior Publication Data

US 2010/0291120 A1 Nov. 18, 2010

(30) Foreign Application Priority Data

Jun. 23, 2006 (EP) .................................... 06013025

(51) Int. Cl.

| | |
|---|---|
| ***C07K 14/725*** | (2006.01) |
| ***A61K 38/00*** | (2006.01) |
| ***A61K 39/39*** | (2006.01) |
| *C07H 21/04* | (2006.01) |

(52) U.S. Cl.
CPC ............ *C07K 14/7051* (2013.01); *A61K 38/00* (2013.01); *A61K 39/39* (2013.01)

(58) Field of Classification Search
None
See application file for complete search history.

(56) References Cited

U.S. PATENT DOCUMENTS 6,197,531 B1 3/2001 Lieberman

FOREIGN PATENT DOCUMENTS

WO WO9622306 A 7/1996
WO WO2005115430 A 12/2005

OTHER PUBLICATIONS

Campbell, A.M. Monoclonal antibody technology, Elsevier Science Publishing Co., Inc., NY, NY, USA, pp. 1-33, 1984.*
Ngo et al. The Protein Folding Problem and Tertiary Structure Prediction, Merz & LeGrand, Birkhauser Boston, pp. 491-495, 1994.*
Hoyer et al (Blood. 2009;113:389-395).*
Zeng et al (J. Clin. Invest. 112:1211-1222, 2003).*
Belkaide and Rouse (Nature Immunol. 6(4): 353-360, 2005).*
Leavy (Nature Reviews: Immunology, 7: 322-323, 2007).*
Reverso (English Definition dictionary/Reverso, 2015, worldwideweb at dictionary.reverso.net).*
UniProt P04234 (2015).*
Database EMBL [Online]; May 25, 1997, "zw70a10.sl Soares_testis-NHT *Homo sapiens* cDNA clone IMAGE:781530 3' similar to gb:X01451_cds1 T-Cell Surface Glycoprotein CD3 Delta Chain Precursor (Human);, mRNA sequence." ; XP02396085 ; retrieved from EBI accession No. EM_EST:AA431288 ; Database accession No. AA431288.
Database EMBL [Online]; Oct. 28, 1998, "qg82f07.x1 Soares_NFL_T_GBC_S1 *Homo sapiens* cDNA clone IMAGE: 1841701 3' similar to gb:X01451_cds1 T-Cell Surface Glycoprotein CD3 Delta Chain Precursor (Human);, mRNA sequence." XP002396086 retrieved from EBI accession No. EM_EST:AI219691 ; Database accession No. AI219691.
Call, Matthew E et al., "The T cell receptor: Critical role of the membrane environment in receptor assembly and function," Ann. Rev. Immunol. 2005, 23:101-125, XP002396081, ISSN: 0732-0582.
Kuhns, Michael S et al., "Deconstructing the form and function of the TCR/CD3 complex," Immunity 2006, 24 (2):133-139, XP002396082, ISSN: 1074-7613.
International Search Report and Written Opinion mailed Dec. 18, 2007 for PCT Application No. PCT/EP2007/005553.

* cited by examiner

*Primary Examiner* — Gerald R Ewoldt
*Assistant Examiner* — Marianne Dibrino
(74) *Attorney, Agent, or Firm* — Faegre Baker Daniels LLP

(57) ABSTRACT

The present invention is related to a peptide comprising an amino acid sequence according to SEQ. ID. No 1.

5 Claims, 12 Drawing Sheets

PEPTIDES REGULATING THE SURFACE EXPRESSION OF THE T CELL RECEPTOR

CROSS REFERENCE TO RELATED APPLICATIONS

This application is a U.S. national stage entry of PCT/EP2007/05553, filed Jun. 23, 2007, which claims priority to European Patent Application No. EP 060 13025.9 filed on Jun. 23, 2006, which is incorporated herein by reference in its entirety.

FIELD

The present invention is related to peptides regulating the surface expression of the T cell receptor as well as cytokine receptors, nucleic acids coding therefor and agents interacting therewith and uses thereof

BACKGROUND

To date, immune-related diseases such as, in particular, infectious diseases and autoimmune disorders are one of the biggest challenges for both human and animal health. The prevention and treatment of this kind of diseases is possible at various levels of the pathogenic mechanism underlying this kind of diseases. One approach is to target the ultimate causative agent which means, in case of infectious diseases, the pathogen and in case of autoimmune disease the respective autoreactive antibodies or lymphocytes. Although this is a reasonable and in quite a number of cases successful approach, however, it still has some drawbacks. These drawbacks are, among others, in case of infectious diseases a shortage of means addressing the pathogen, in particular when it comes to viruses, and an increasing number of resistant strains of various bacteria against a number of antibiotics available for the time being, and in case of autoimmune disorder, the need for constant removal or at least neutralization of autoimmune antibodies or autoreactive immune cells with the autoimmune antibodies being the last element of a cascade and thus being rather abundant requiring a therapeutic approach which is also adequate in terms of titres of neutralizing agents needed.

A quite opposite approach for the treatment of this kind of diseases is to modify the immune system such as to treat or even prevent this kind of diseases. The more upstream an immune system modifying agent is active, the broader its potential field of use is. One such element which is a preferred molecule of consideration insofar, is the T cell receptor (TCR) as described in M. M. Davis, J. J. Boniface, Z. Reich, D. Lyons, J. Hampl, B. Arden, and Y. Chien: Ligand recognition by alpha beta T cell receptors *Annu. Rev. Immunol.* 1998. 16: 523-544.

A high level of TCR expression on T lymphocyte surfaces is required in most infections for complete removal of the pathogen. The particular relevance of T cell receptor expression insofar is further illustrated by the fact that it takes ten times more low avidity T cells to control infection than high avidity T cells which is particularly important for the development of vaccines as described by Derby, M., Alexander-Miller, M., Tse, R., and Berzofsky, J: High-avidity CTL exploit two complementary mechanisms to provide better protection against viral infection than low-avidity CTL. *J Immunol* 2001. 166: 1690-1697. The low surface display of antigenic peptides during some virus infection such as, e.g., human immune deficiency virus (HIV) or by hepatitis C virus (HCV) shows that high avidity T cells are needed to protect from infections after vaccination. On the other hand, in autoimmune diseases, obviously, self-antigens are over-recognized by such T cell receptor which, in turn, triggers an over boarding immune response with severe concomitant physiological responses. Insofar, for this kind of disease a blocking of increased surface expression of T cell receptors is highly desirable.

A problem underlying the present invention was thus to provide means for the treatment of immune-related diseases, and more particularly for the treatment and/or prevention of infections and/or autoimmune disorders. In a further aspect, the present invention was to provide means for increasing the T cell receptor expression on T lymphocytes.

BRIEF DESCRIPTION OF THE DRAWINGS

The present invention shall now be further illustrated by reference to the following drawings and examples from which as well as from the sequence listing, further advantages, features and embodiments may be taken.

FIG. 1A shows the result of an analysis of CD3delta RT-PCR samples from T cell cultures raised against cross-reactive peptides 16 and 23 after 4 h stimulation, whereby mRNA from human spleen is used as control;

FIG. 1B shows the result of an analysis of CD3delta RT-PCR samples from freshly isolated PBMCs from healthy donors and from patients with autoimmune diseases, whereby RA means rheumatoid arthritis with lymphocytes having been isolated from knee effusions of three patients; GBS means three patients with Guillian-Barré-Syndrom; CIDP means three patients with chronic inflammatory demyelating polyneuropathy;

FIG. 1C shows the result of a CD3delta RT-PCR of T cell cultures against heteroclitic peptides which were generated with dendritic cells, IL-2, IL-7 and IL-15, whereby the cell cultures have been stimulated for 4 h with the culture peptide or left untreated.

DETAILED DESCRIPTION

Figures 1A, 1B, 1C, 1D:
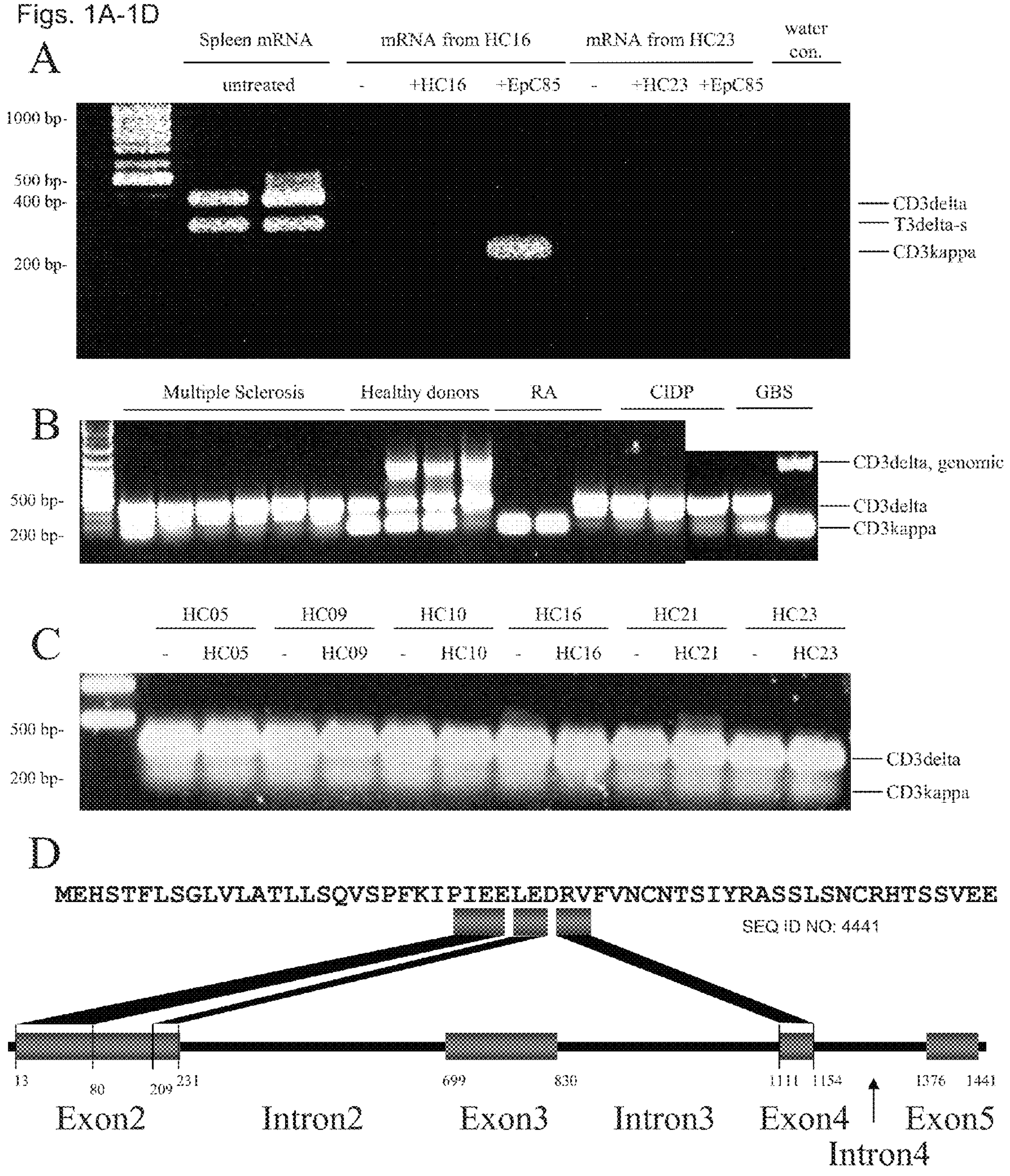
FIGS. 1A to C show a CD3delta RT-PCR visualizing the result of an expression analysis of CD3 delta splice variants, whereby more specifically
FIG. 1D shows the genomic sequence organization of CD3delta and of the derived splice variant CD3 kappa (SEQ. ID. No. 4441), which is a signal peptide linked to SEQ ID NO:4.

In a first aspect the problem underlying the present invention is solved by a peptide comprising an amino acid sequence according to SEQ ID NO:1.

In an embodiment the peptide comprises at least an amino acid sequence encoded by at least one exon of the CD3 gene complex or part thereof.

In a preferred embodiment the amino acid sequence is encoded by exons 2 and 4 of the CD3 gene.

In a second aspect the problem underlying the present invention is solved by a peptide comprising an amino acid sequence according to SEQ ID NO:4.

In an embodiment of the first and the second aspect the peptide increases or prolongs the expression of the T cell receptor.

In a preferred embodiment of the first and the second aspect the expression is the expression of the T cell receptor on the cell surface of T cells, more specifically on the cell surface of T lymphocytes.

In an embodiment of the first and second aspect the peptide blocks or reduces internalization of the T cell receptor.

In an embodiment of the first and second aspect the peptide increases the expression of a compound selected from the group comprising CD4, CD2, CD25, CD116, CD127, CCR5, CCR9, CXCR1, CXCR3, EGF, Eotaxin-2, I-309, IFN-gamma, IL-1 alpha, IL-1 beta, IL-3, IL-6, NAP-2, TGF-beta3, and PARC.

In an embodiment of the first and second aspect the peptide decreases the expression of a compound selected from the group comprising CD58, IL-1ra, IL-8, RANTES, SDF-1, TARC, MCP-4, GRO, soluble IL-6 receptor and soluble TNF-receptor II.

In an embodiment of the first and second aspect the peptide is labelled, preferably by having incorporated a labelled amino acid, whereby more preferably the labelled amino acid is radioactively labelled with tritium, C-14, I-125 or S-35; or whereby the labelled amino acid is labelled with a NMR-active isotope, most preferably with deuterium, C-13 or N-15.

In an embodiment of the first and second aspect the peptide further comprises a moiety which is suitable for detection using a method for detection, whereby such moiety is preferably selected from the group comprising fluorophores, radioactive tracers and haptens, whereby preferably the hapten is biotin.

In a third aspect the problem underlying the present invention is solved by a complex comprising a peptide selected from the group comprising a peptide according to any of claims 1 to 11, and a receptor molecule selected from the group comprising the T-cell receptor, CD4, CD2, CD25, CD127, CCR5, CCR9, CXCR1, CXCR3 and the GM-CSF receptor (CD116).

In a fourth aspect the problem underlying the present invention is solved by a nucleic acid coding for a peptide according to the first and second aspect.

In an embodiment of the fourth aspect the nucleic acid comprises a nucleic acid sequence according to SEQ ID NO:2 or SEQ ID NO:3, or a derivative thereof.

In a preferred embodiment of the fourth aspect the derivative is a nucleic acid (a) which is essentially complementary to the nucleic acid sequence according to SEQ ID NO:2 or to SEQ ID NO:3; or
(b) which hybridises to the nucleic acid sequence according to the nucleic acid sequence according to SEQ ID NO:2 or to SEQ ID NO:3; or
(c) which, but for the degeneracy of the genetic code, would hybridise to the nucleic acid of (a) or (b).

In a more preferred embodiment of the fourth aspect the hybridisation is a hybridisation under stringent conditions In a fifth aspect the problem underlying the present invention is solved by a vector comprising a nucleic acid according to the fourth aspect, whereby the vector is preferably an expression vector.

In an embodiment of the fifth aspect the vector is selected from the group comprising mammalian, microbial, insect and viral vectors.

In a sixth aspect the problem underlying the present invention is solved by a host cell comprising a nucleic acid according to the fourth aspect and/or a vector according to the fifth aspect.

In an embodiment of the sixth aspect, the host cell is an animal cell, preferably a mammalian cell.

In a preferred embodiment of the sixth aspect if the mammalian cell is a human cell, such human cell is an in vitro human cell.

In a seventh aspect the problem underlying the present invention is solved by an organism comprising a host cell according to the sixth aspect, whereby the organism is a non-human animal, preferably a non-human mammal.

In an eighth aspect the problem underlying the present invention is solved by a method for producing a peptide according to the first and second aspect, comprising the following steps:

(a) cultivating a cell according to the sixth aspect in a medium under conditions which allow the production of the peptide; and
(b) harvesting the peptide; and
(c) optionally purifying the peptide.

In a ninth aspect the problem underlying the present invention is solved by the use of a peptide according to the first and second aspect for the manufacture of a medicament.

In a tenth aspect the problem underlying the present invention is solved by the use of a nucleic acid according to the fourth aspect for the manufacture of a medicament.

In an embodiment of the ninth and tenth aspect the medicament is for the treatment and/or prevention of a disease, whereby such disease goes along or is associated with a decreased T cell receptor expression.

In an embodiment of the ninth and tenth aspect the medicament is for the treatment and/or prevention of a disease, whereby such disease goes along or is associated with a decreased expression of a compound selected from the group comprising CD4, CD2, CD25, CD116, CD127, CCR5, CCR9, CXCR1, CXCR3, EGF, Eotaxin-2, I-309, IFN-gamma, IL-1alpha, IL-1 beta, IL-3, IL-6, NAP-2, TGF-beta3, and PARC.

In an embodiment of the ninth and tenth aspect the medicament is for the treatment and/or prevention of a disease, whereby such disease goes along or is associated with an increased expression of a compound selected from the group comprising CD58, IL-1ra, IL-8, RANTES, SDF-1, TARC, MCP-4, GRO, soluble IL-6 receptor and soluble TNF-receptor II.

In a preferred embodiment of the ninth and tenth aspect the disease is selected from the group comprising infectious diseases.

In a more preferred embodiment of the ninth and tenth aspect the disease is selected from the group comprising HIV infection and hepatitis C infection.

In an embodiment of the ninth and tenth aspect the medicament is for the treatment and/or prevention of a disease, whereby such disease is a disease associated with or caused by an increased expression of the T cell receptor, preferably an increased expression of the T cell receptor on the surface of T lymphocytes, and more preferably such disease is selected from the group comprising autoimmune diseases.

In a preferred embodiment of the ninth and tenth aspect the disease is selected from the group comprising rheumatoid arthritis.

In an embodiment of the ninth and tenth aspect the medicament is for immuno-compromised or immuno suppressed patients.

In an embodiment of the ninth and tenth aspect the medicament is for patients suffering from T cell depletion.

In a preferred embodiment of the ninth and tenth aspect the T cell depletion is a drug induced T cell depletion, preferably a T cell depletion induced by a chemotherapeutic agent.

In an embodiment of the ninth and tenth aspect the patients are subject who have or will undergo transplantation.

In an eleventh aspect the problem underlying the present invention is solved by the use of a peptide according to the first and second aspect as and/or for the manufacture of an adjuvant.

In a twelfth aspect the problem underlying the present invention is solved by the use of a nucleic acid according to the fourth aspect as and/or for the manufacture of an adjuvant.

In an embodiment of the eleventh and twelfth aspect the adjuvant is for use in vaccination, preferably in vaccination against poorly immunogenic antigens.

In a thirteenth aspect the problem underlying the present invention is solved by a method for the screening of an agent for the development and/or manufacture of a medicament for the treatment and/or prevention of a disease and/or for the development and/or manufacture of a diagnostic agent for the diagnosis of a disease, whereby the disease is a disease as defined in any of the preceding aspects and any pathological conditions an overexpression or underexpression of the T cell receptor, comprising the steps:

a) providing a candidate compound,
b) providing an expression system for the peptide according to the first and second aspect and/or a system detecting the activity of such peptide;
c) contacting the candidate compound with the expression system for said peptide and/or the system detecting the activity of said peptide;
d) determining if the expression and/or the activity of said peptide is changed under the influence of the candidate compound.

In an embodiment of the thirteenth aspect the candidate compound is contained in a library of compounds.

In an embodiment of the thirteenth aspect the candidate compound is selected from the group of classes of compounds comprising peptides, proteins, antibodies, anticalines, functional nucleic acids, natural compounds and small molecules.

In a preferred embodiment of the thirteenth aspect the functional nucleic acids are selected from the group which comprises aptameres, aptazymes, ribozymes, spiegelmers, antisense oligonucleotides and siRNA.

In a fourteenth aspect the problem underlying the present invention is solved by the use of a peptide according to the first and second aspect or a part or derivative thereof and/or nucleic acid or a part or derivative thereof coding for said peptide or a part or a derivative thereof as target molecule for the development and/or manufacture of a medicament for the treatment and/or prevention of a disease and/or for the development and/or manufacture of a diagnostic agent for the diagnosis of a disease, whereby the disease is a disease as defined in any of the proceeding aspects.

In an embodiment of the fourteenth aspect the medicament and/or the diagnostic agent comprises an agent, which is selected from the group comprising antibodies, peptides, anticalines, small molecules, antisense molecules, aptameres, spiegelmers and RNAi molecules.

In a preferred embodiment of the fourteenth the agent interacts with the peptide according to the first and second aspect.

In an embodiment of the fourteenth the agent interacts with the nucleic acid coding for the peptide according to the first and the second aspect or a part or derivative thereof, in particular with mRNA, genomic nucleic acid or cDNA for said peptide.

In a fifteenth aspect the problem underlying the present invention is solved by the use of a polypeptide which interacts with the peptide according to the first and second aspect or a part or derivative thereof, for the development or manufacture of a medicament for the treatment and/or prevention of a disease and/or for the development and/or manufacture of a diagnostic agent for the diagnosis of a disease, whereby the disease is a disease as defined in any of the preceding aspects.

In an embodiment of the fifteenth aspect the polypeptide is selected from the group, which comprises antibodies against said peptide or a part or derivative thereof and polypeptides binding said peptide or a part or derivative thereof.

In a sixteenth aspect the problem underlying the present invention is solved by the use of a nucleic acid which interacts with a peptide according to the first and second aspect or a part or derivative thereof, for the development or manufacture of a medicament for the treatment and/or prevention of a disease and/or for the development and/or the manufacture of a diagnostic agent for the diagnosis of a disease, whereby the disease is a disease as defined in any of the preceding claims.

In an embodiment of the sixteenth aspect the nucleic acid is selected from the group which comprises aptamers and spiegelmers.

In a seventeenth aspect the problem underlying the present invention is solved by the use of a nucleic acid which interacts with a nucleic acid coding for a peptide according to the first and second aspect or a part or derivative thereof, for the development and/or manufacture of a medicament for the treatment and/or prevention of a disease and/or for the development and/or manufacture of a diagnostic agent for the diagnosis of a disease, whereby the disease is a disease as defined in connection with the first and second aspect.

In an embodiment of the seventeenth aspect the interacting nucleic acid is an antisense oligonucleotide, a ribozyme and/or siRNA.

In an embodiment of the seventeenth aspect the nucleic acid coding for the peptide or a part or derivative thereof is the cDNA, mRNA or hnRNA.

In an embodiment of the fourteenth to seventeenth aspect the disease is a disease associated with or caused by an increased expression of the T cell receptor, preferably an increased expression of the T cell receptor on the surface of T lymphocytes, and more preferably such disease is selected from the group comprising autoimmune diseases.

In an eighteenth aspect the problem underlying the present invention is solved by a pharmaceutical composition comprising at least one agent selected from the group comprising the peptide according to the first and second aspect or a part or derivative thereof, small molecules interacting with the peptide according to the first and second aspect or a part or derivative thereof or with a nucleic acid coding for the peptide according to the first and second aspect or a part or derivative thereof, antibodies specific for the peptide according to the first and second aspect or a part or derivative thereof, polypeptides interacting with the peptide according to the first and second aspect or a part or derivative thereof, a nucleic acid coding for the peptide according to the first and second aspect or a part or derivative thereof, nucleic acids interacting with the peptide according to the first and second aspect or a part or derivative thereof or nucleic acids interacting with a nucleic acid coding for the peptide according to the first and second aspect or a part or derivative thereof, and at least one pharmaceutically acceptable carrier, preferably for the prevention and/or the treatment of a disease whereby the disease is a disease as defined in any of the preceding claims.

In a nineteenth aspect the problem underlying the present invention is solved by a kit for the characterisation of a disease or a condition as defined in any of the preceding claims, comprising at least one agent which is selected from the group comprising the peptide according to the first and second aspect or a part or derivative thereof, antibodies specific for the peptide according to the first and second aspect or a part or derivative thereof, polypeptides interacting with the peptide according to the first and second aspect or a part or derivative thereof, polypeptides interacting with a nucleic acid coding for the peptide according to the first and second aspect or a part or derivative thereof, nucleic acids interacting with the peptide according to the first and second aspect or a part or derivative thereof, nucleic acids interacting with a nucleic acid coding for the peptide according to the first and second aspect or a part or derivative thereof, and optionally at least one other compound.

The present inventors have surprisingly found that the sensitivity and function of T lymphocytes to antigenic stimulation can be increased by a peptide which is referred to herein as CD3 kappa and its derivatives. Also, the present inventors have surprisingly found that CD3 kappa is suitable to improve the surface expression of the T cell receptor on the surface of cells. Finally the present inventor has found that CD3 kappa has a direct or indirect impact on the expression of distinct Cytokines and/or Chemokines, and on the expression of some Chemokine and/or Cytokine-Receptors.

More particularly, the present inventors have found a new splice variant of CD3 providing a new open reading frame comprising the amino acid sequence according to SEQ ID NO. 1. This open reading frame encodes a peptide which is responsible for changing the characteristics and biological behaviour of the splice variant of CD3 disclosed herein. This peptide has the amino acid sequence according to SEQ ID NO:4 and is referred to as CD3 kappa or CD3 kappa peptide. Without wishing to be bound by any theory, the peptide encoded by this new open reading frame and the CD3 kappa peptide, respectively, seems to avoid the internalization of the T cell receptor thus being, either directly or indirectly, involved in the improved, this is to say increased and/or prolonged surface expression of the T cell receptor. The peptide which is encoded by said new open reading frame is also referred to herein as CD3 kappa-ORF. Said CD3 kappa-ORF forms the C terminal part of CD3 kappa peptide having the amino acid sequence according to SEQ ID NO. 4. CD3 kappa is another splice variant of CD3 delta. Compared to CD3 delta, however, CD3 kappa is lacking exon 3 and a part of exon 2 but contains the entire exons 1, 4 and 5. CD3 kappa is in particular expressed by peripheral blood leukocytes, optionally along with other CD3 delta isoforms. CD3 kappa is, again without wishing to be bound by any theory, suitable to increase the sensitivity of T lymphocytes to antigenic stimulation, whereby such increased sensitivity seems to be based on an improved expression and/or surface display of the TCR on T lymphocytes. Also, CD3 kappa is, without wishing to be bound by any theory, suitable to provide for an improved expression of the TCR on T lymphocytes, more specifically on the surface of T-lymphocytes.

CD3 kappa also, moreover without wishing to be bound by any theory, has a direct or indirect effect on the expression of distinct Cytokines and/or Chemokines, and on the expression of some Chemokine and/or Cytokine-Receptors. More specifically CD3 kappa leads to an increased release of proinflammatory cytokines and chemokines, most specifically of EGF, Eotaxin-2, I-309, IFN$\gamma$, IL-1$\alpha$, IL-1$\beta$, IL-3, IL-6, NAP-2, TGF$\beta$3 and PARC; while CD3 kappa induces a decreased release of IL-1ra, IL-8, RANTES, SDF-1, TARC, MCP-4, GRO, soluble IL-6 Receptor and soluble TNF-Receptor II by peripheral blood mononuclear cells. The described changes in secretion occur more specifically after about 24 h upon addition of CD3 kappa and last for up to eight days in vitro. CD3 kappa leads to an up-regulation of CD4 and CD2, and of some Chemokine and Cytokine-Receptors, more specifically of Cytokine/Chemokine-Receptors which lead to anti-apoptotic and/or proliferation inducing effects. Most specifically CD3 kappa leads to an up-regulation of CD25, CD116, CD127, CCR3, CCR9 and CXCR1. CD3 kappa also leads to a slight upregulation of CXCR3 and CXCR4.

As preferably used herein, the term “improved expression” or “upregulation” shall, in a preferred embodiment, mean that the expression of the TCR and of the Cytokine/Chemokine-receptors is increased, whereby such increase in expression can be, alternatively or additionally, a prolonged expression of the individual receptor or an increase of the number of individual receptors preferably by increased translation and/or transcription. More preferably, the lifetime of the expression of the individual receptor is increased.

In a preferred embodiment the term “surface expression” or “up-regulation” shall be the presence of the TCR and of the Cytokine/Chemokine-receptors on a surface of a cell. Preferably, the cell is a mammalian cell and more preferably the cell is an immune and/or hematopoetic cell, e.g., a T lymphocyte and most preferably the cell is a CD4+ T lymphocyte.

In a preferred embodiment, the T cell receptor is the human T cell receptor and is, for example, described in M. M. Davis, J. J. Boniface, Z. Reich, D. Lyons, J. Hampl, B. Arden, and Y. Chien: Ligand recognition by alpha beta T cell receptors *Annu. Rev. Immunol.* 1998. 16: 523-544.

The term “surface” as preferably used herein refers to a surface present either on the outside of the cell or on the boundary of a cell which is preferably formed by a cytoplasm membrane separating the cytoplasm of a cell from the environment around a cell, or to rapidly exchanged or exchanging membrane compartments which are preserved in intracellular compartments e.g. endosomes or lysosomes, in which parts of the cytoplasm membrane is recycled or recycling. Most preferably the term "surface" refers to lipid rafts in the cytoplasm membrane.

The T cell receptor is an alpha:beta-heterodimer consisting of one T cell receptor-alpha chain and one T cell receptor-beta (TCR beta) chain. About 30,000 molecules of this kind of T cell receptors are present on a normal human T cell. Apart from the alpha:beta T cell receptor, there is also a subpopulation of T cells with a T cell receptor which is different from the alpha:beta T cell receptor and consists of a heterodimer of gamma- and delta chains. In connection with the present invention, these gamma:delta-T cell receptors or other theoretically possible heterodimeric receptors consisting of two of these four chains are comprised by the term alpha:beta-T cell receptors which is, in turn, generally referred to as T cell receptor or TCR.

Also, the term T cell receptor shall comprise the T cell receptor complex, if not explicitly stated to the contrary. Such T cell receptor complex comprises apart from the T cell receptor in the narrower sense, i.e., consisting of the alpha: beta-heterodimer, also in general four CD3 molecules or functional homologous molecules, namely gamma, delta, epsilon, eta and also zeta, whereby CD3 epsilon forms a complex with either the CD3 delta or the CD3 gamma chain. CD3 zeta can be a homodimer or a Heterodimer with CD3 eta or other molecules. However the lack of one or more CD3 chains is possible, including any variations as found by different splicing. It will be acknowledged that other factors may be comprised by the T cell receptor complex and thus by the T cell receptor as used herein.

In a preferred embodiment the term that "the expression of the T cell receptor is increased", refers to the result of a comparison made between the T cell receptor in a patient with CD3 kappa and a healthy subject without CD3 kappa. A patient is preferably a diseased subject or a subject suspected of suffering from a disease or a subject being prone to such disease. A healthy subject preferably is either the same or a different subject not being diseased or not being prone to be diseased or a group of persons not diseased or not being prone to be diseased. The comparison is made between a patient and a healthy subject, whereby the measures needed insofar are preferably commonly known to the ones skilled in the art. Preferably such measures comprise obtaining a sample from the patient and healthy subject, respectively. Preferably such sample is a blood sample or effusions from inflamed tissues such as, e.g., the knee. In case of healthy subjects such samples may be taken at any time. In case of patients such samples are preferably taken prior, during and after the treatment. Such frequent sampling also allows for a staging of the disease as well as a monitoring and deciding whether the therapy used is actually effective. In case of patients who received high doses of myelotoxic chemotherapy or who undergo therapy with biologicals are most preferably taken when these patients are reconstituted in blood formation with leukocyte values around or above 1/nl. The isolated mononuclear cells are incubated with CD3 kappa for 1 to 6 days and tested for the ability of CD3 kappa to improve the function of leukocytes as described below. This diagnostic approach shows whether an immune defect is actually present which is treatable with CD3 kappa. In a further step, the comparison comprises the determination of the expression of the TCR. The expression of the TCR can be determined by various means, preferably on T-lymphocytes of the patient and healthy subject, respectively, and more particularly on the samples obtained there from. Among others, and not limited thereto, the expression can be determined by using compounds specifically interacting with the TCR. Such specifically interacting compounds are preferably selected from the group comprising antibodies, high affinity binding peptides, anticalines, aptamers and spiegelmers. For purpose the expression of the cytokines and chemokines, respectively, and the cytokine/chemokine receptors described herein as being related to or associated with the TCR expression, are analysed as well. This will show an improvement of function of leukocytes in general by bystander effects e.g. by secretion of factors or more specially of the herein described cytokines by the CD3 kappa modulated mononuclear cells. The expression of Cytokine/Chemokine-receptors and the expression of distinct Cytokines and/or Chemokines can be assessed on mononuclear cells. This expression analysis is preferably done by flow-cytometric analysis and leads to Mean-Fluorescence indices (MFI), which are direct proportional to the TCR or the Cytokine/Chemokine-receptor expression strength. The release of Cytokines and/or Chemokines can be determined by the use of specific antibodies which are labelled or which lead to the enzymatic generation of measurable products. Alternatively, the expression of the TCR, of the said other receptors or of the said cytokines can be determined by functional assays, whereby such functional assays preferably comprise the following steps: Cell culture of lymphocytes followed by peptide stimulation and analysis of cytokine expression with cytokine specific antibodies. Preferably, the expression between a patient and a healthy person is increased by a value of at least 10%, 20%, 50%, 100% or more. This increase depends on the basal TCR expression in the patient and might range from 20% in healthy individuals to 2500% in patients with severe compromised immune function after high doses of chemotherapy and therapy with biologicals. This percentage may refer as a measure to the number of T cell receptors present on a surface or the time an individual T cell receptor is available on such surface, whereby it is to be acknowledged that the time may be the average time of a group of T cell receptors or the average time of the T cell receptor on a group of lymphocytes, preferably the lymphocytes contained in the sample or a fraction thereof. More specifically, the incubation time is at least 4 hours to enable recycling of TCRs from various cellular compartments. The increase in the expression of the above named Cytokine/Chemokine-receptors and the said cytokines is analyzed in the same way. It will be understood by the ones skilled in the art that the samples are standardized in a preferred embodiment.

In a preferred embodiment, the difference in TCR expression between a patient population with MFIs below 22 and healthy subjects with a MFI around 115 is by a factor of 6, whereby such difference is preferably observed within 24 hours after in vitro culture and preferably lasts for at least two days, preferably at least four days and more preferably at least six days. The difference in the patients and the healthy subjects corresponds to the mean value of TCR expression of the healthy subjects plus five times the standard deviation, making the difference statistically highly significant. In a similar way, the CD4-receptor expression is different between a patient population and healthy subjects. However in the case of CD4, the difference is visible preferably after six days after in vitro culture.

Most patients with higher TCR expression as the patients described above show a MFI around 45 which correspond to a difference to the mean value of TCR expression of the healthy subjects plus three times the standard deviation and is still a statistically significant reduced TCR expression as compared to the healthy subjects. In a similar way as particularly described in the previous paragraph, the difference of TCR- and/or CD4-receptor expression is visible after in vitro culture as described this paragraph.

The present inventors have found that in the described patient populations the expression of the TCR in the T lymphocytes can be increased in a statistically significant manner by CD3 kappa and its derivatives to normal values as defined by healthy individuals. As will be outlined in more detail herein, such increase can be used for or is the basis of any treatment and/or prevention of diseases which are characterized by or associated with a decreased TCR level, preferably TCR level on the T lymphocytes. However also the expression of the said cytokines, more preferably of Th1-cytokines and most preferably of IFNγ can be increased in a statistically significant manner by CD3 kappa and its derivatives to normal values as defined by healthy individuals.

Preferably, the increase in TCR, CD4- and/or CD2-expression after CD3k CD3 kappa peptide treatment can be detected in an in vitro culture at peptide concentrations higher than 1-10 μg/ml, more preferably at concentrations of 10-100 μg/ml, even more preferably at concentrations of 100-500 μg/ml and most preferably at concentrations of 500-2000 μg/ml or even higher concentrations. The upregulation can be detected within 48 hours and is by at least a factor of 50%, more preferably at least 100% and even more preferably at least 200% as compared to the respective negative control. This expression analysis is preferably done by flow-cytometric analysis as described above. Alternatively, the expression of the TCR can be determined by functional assays, whereby such functional assays preferably comprise the following steps: Cell culture of lymphocytes followed by peptide stimulation and analysis of cytokine expression with cytokine specific antibodies. The expression of Cytokine/Chemokine-receptors and the expression of distinct Cytokines and/or Chemokines can be assessed on mononuclear cells in the same way. In another embodiment, the increase in TCR, CD4- and/or CD2-expression is by a factor of at least 2, preferably at least 4 and more preferably at least 6 fold, preferably each within 48 hours, whereby the respective lymphocytes used for the assessment from patients recovering from treatment with T-cell toxic chemotherapeutic agent, whereby preferably the agent is fludarabine and/or alemtuzumab. The increase in TCR, CD4- and/or CD2-expression described should preferably be shown at a concentration of 5-1000 μg/ml peptide versus no peptide or versus a control peptide with random sequence. Most preferably the increase in TCR, CD4- and/or CD2-expression described should be shown at a concentration of 0.5-1 mg/ml CD3kappa peptide versus no peptide or versus a control peptide with random sequence.

The term CD3 kappa or CD3 kappa peptide as used herein also comprises derivatives of the peptide having SEQ ID NO. 4, as obvious for the one skilled in the art. Insofar the term CD3 kappa peptide or CD 3 kappa peptides comprise, in a preferred embodiment of the present invention CD3 kappa having the amino acid according to SEQ ID NO:4 and any derivative thereof, preferably any derivative as defined and/or disclosed herein. A derivative of CD3 kappa as preferably used herein is any peptide preferably having at least one of the characteristics of CD3 kappa having the amino acid sequence according to SEQ ID NO. 4. More specifically, such characteristic is any of the characteristics described herein for CD3 kappa and more preferably described for CD3 kappa having an amino acid sequence according to SEQ ID NO:4. More preferably, such characteristic is the capability to increase the TCR, CD4- and/or CD2-expression within 24 hours by a factor of at least 25%, more preferably at least 50%, even more preferably at least 100% and most preferably 200%. Preferably, such increase in the TCR, CD4- and/or CD2-expression within 24 hours should be observable at peptide concentrations higher than 1-10 μg/ml, more preferably at concentrations of 10-100 μg/ml, even more preferably at concentrations of 100-500 μg/ml and most preferably at concentrations of 500-2000 μg/ml or even higher concentrations. One of the assays in principle useful to determine this or similar characteristics of CD3 kappa in general and the derivatives of CD3 kappa having the amino acid sequence according to SEQ ID NO. 4 in particular, is described in the attached examples, whereby other or different assays are either known to the one skilled in the art or will be obvious for the one skilled in the art in the light of the present disclosure.

In principle, the derivatives of CD3 kappa and in particular of CD3 kappa having the amino acid sequence according to SEQ ID NO:4 can be divided into the following groups: full-length derivatives, truncated derivatives and modified derivatives.

Full-length derivatives have the same length as the CD3 kappa peptide according to SEQ ID NO:4 or comprise the complete amino acid sequence of CD3 kappa having the amino acid sequence according to SEQ ID NO:4. Full-length derivatives are characterized by one or several changes made to at least one or several amino acids forming the peptide. Such changes are preferably related to the side-chain of the amino acid. However, it is also within the present invention that a full-length derivative has the same sequence of side-chains but the backbone forming entities such as amino acids or derivatives thereof is changed, i.e. different from the peptide backbone obtained or observed when two or more amino acids are covalently linked to each other through a peptide bond whereby this kind of compound belongs to the group called peptidomimetics, which are formed e.g. through exchange of the amide-peptide-binding by urea resembling so called 'ureidopeptides' as shown by Barth B S, Myers A C and Lipton M A.: Exploring the stereochemical requirements for protease inhibition by ureidopeptides. *J Pept Res.* 2005 March; 65(3):352-4; or through exchange of the amide-peptide-binding by thioamide-linkage yielding Endothiopeptides as shown by Yao S, Zutshi R and Chmielewski J.: Endothiopeptide inhibitors of HIV-1 protease. *Bioorg Med Chem. Lett.* 1998 Mar. 17; 8(6):699-704. Such non-peptide backbone can be present in the derivative either only for one building block or for several of the building blocks forming the derivative or, by reference to the CD3 kappa peptide having the amino acid sequence according to SEQ ID NO:4, for one or several of the amino acids, including the complete backbone thereof. This kind of modification is preferably used to reduce enzyme degradation in vivo or improve peptide binding which has been shown e.g. by Abdel-Rahman H M, Kimura T, Hidaka K, Kiso A, Nezami A, Freire E, Hayashi Y, Kiso Y.: Design of inhibitors against HIV, HTLV-I, and *Plasmodium falciparum* aspartic proteases. *Biol. Chem.* 2004 November; 385(11):1035-9.

The term full-length derivative also comprises derivatives which contain the full-length amino acid sequence of the CD3 kappa peptide according to SEQ ID NO:4 and one or several further or additional amino acids, whereby such further amino acids are additionally or alternatively attached to the N-terminus or to the C-terminus. Furthermore, each of the further amino acid(s) can be attached to any of the side-chain of the amino acids and building blocks, respectively, forming the derivative of the CD3 kappa peptide according to SEQ ID NO:4. It is also within the present invention that this kind of full-length derivatives comprises at one or several amino acid positions, relative to the amino acid sequence according to SEQ ID NO:4, one or several amino acids or further building blocks incorporated into the amino acid sequence, more specifically, the backbone of the respective amino acid sequence, whereby the backbone is preferably a peptide backbone. Also, the full-length derivative is in an embodiment a modified derivative, preferably a modified derivative as defined herein. It is also within the present invention that the embodiments described in the present section are embodiments of the derivatives described in the preceding section.

The full-length derivatives of the CD3 kappa peptide comprising changes in the amino acid sequence relative to the sequence of CD3 kappa having the amino acid sequence according to SEQ ID NO:4 at one or several positions, preferably without that such derivative lacks one of the characteristics of a CD3 kappa peptide as defined herein, are preferably characterized in that an amino acid of a distinct category is replaced by another amino acid of the same category. Such categories are preferably neutral amino acids, aliphatic amino acids, cationic amino acids, anionic amino acids, thiol-containing amino acids, aromatic amino acids and heterocyclic amino acids. As peptides may be obtained by protocols of organic synthesis, amino acid replacements are not limited to those of proteinogenic amino acids. Any building block including, but not limited to, non-proteinogenic amino acids, beta-amino acids, D-amino acids and L-amino acids or completely synthetic amino acids or amino acid like compounds like the transition state mimetic allophenylnorstatine that may be incorporated by suitable chemical procedures, may be included in the peptide.

To the extent the full-length derivatives of the CD3 kappa are generated by the exchange of one or several of the amino acids of the CD3 kappa peptide having the amino acid sequence according to SEQ ID NO:4, the peptides having SEQ ID NO. 5-4417 are disclosed herein as exemplary full-length derivatives of the CD3 kappa peptide.

Truncated derivatives of the CD3 kappa peptide are peptides comprising a part of the amino acid sequence of the CD3 kappa peptide and its derivatives, in particular the full-length derivatives. In an embodiment the truncated derivative exhibit the changes described above for the full-length derivatives, whereby the overall length of the truncated derivative is shorter, at least by one amino acid or a building block compared to the CD3 kappa according to SEQ ID NO:4 and the full-length derivatives, preferably the full-length derivatives described herein. In a further embodiment these truncated derivatives preferably comprise a core sequence of as little as 12 amino acids, preferably 18 amino acids and more preferably 25 amino acids. The sequence of this kind of truncated derivatives may start, in terms of N-terminal end, at the N-terminus or any other position relative to the full length sequence of CD3 kappa having the amino acid sequence according to SEQ ID NO:4 or any of the full-length derivatives described herein.

To the extent the derivatives of the CD3 kappa are generated by truncating the amino acid sequence of CD3 kappa having the amino acid sequence according to SEQ ID NO:4 and of the full length derivatives thereof, preferably as disclosed herein, the peptides having SEQ ID NO. 4418-4437 are disclosed herein as exemplary truncated derivatives thereof.

A modified derivative is any derivative of the CD3 kappa peptide having the amino acid sequence according to SEQ ID NO:4, of any full-length derivative or of any truncated derivative exhibiting at least one further modifying group. Such modifying group can be present at or attached to the N-terminus, the C-terminus or any of the amino acids or building blocks, including any side chain thereof, forming the CD3 kappa peptide having the amino acid sequence according to SEQ ID NO:4, any full-length derivative thereof or any truncated derivative thereof. In a preferred embodiment, the modifying group is different from an amino acid or any of the building blocks forming the CD3 kappa peptide having the amino acid sequence according to SEQ ID NO:4, any full-length derivative thereof or any truncated derivative thereof. More preferably, the modifying group is selected from the group comprising acetate group, phosphor group and sugar group, more preferably glucose group. Most preferably the modifying sugar groups as N-acetyl-D-glucosamine or N-acetyl-D-galactosamine are attached to one or more serine residues at positions 1, 4 24, 29, 30, 32 38 and/or 39, and/or to the threonine residue at position 23, and/or to one or more asparagine residues at positions 20, 22 and/or 33. The modifying sugar groups include oligo- and polyglycans.

It is to be acknowledged by the one skilled in the art that in a preferred embodiment additionally or alternatively a peptide having homology of at least 80%, 85%, 90%, 95%, 96%, 97%, 98% or 99% compared to either the CD3 kappa peptide according to SEQ ID NO:4, any full-length derivative thereof or any truncated derivative thereof shall be regarded as a derivative of CD3 kappa, preferably under the proviso that the derivative and/or the peptide to which is referred for the purpose of comparison, still exhibits at least one of the characteristics of the CD3 kappa peptide according to SEQ ID NO:4.

In a preferred embodiment the CD3 kappa peptide further comprises a moiety which is suitable for detection. More specifically, such moiety allows for the detection of the peptide and/or any receptor interacting therewith. The moiety may be any group suitable for such purpose. Respective moieties are known to the one skilled in the art and comprise, however, are not limited to, fluorophors such as for example carboxyfluorescein or biotin. Preferably, the detection is caused by means of fluorescence. Alternatively, the detection may also occur by means of radioactivity, e.g. after incorporation of tritium, C-14, I-125 or S-35 by protocols known to the one skilled in the art. Detection may occur at the level of an individual cell, a tissue, an organ or an animal. Preferably the animal is a mammal and more preferably selected from the group comprising dog, cat, sheep, goat, rat, mouse, cow, horse and a human being. Detection may occur in vitro, in situ, in vivo, and/or ex vivo.

CD3 kappa peptide also comprises a moiety which is suitable for detection and/or determination of the molecular structure and/or of biochemical properties. Labelling might be done by incorporation of NMR-active isotopes, most preferably deuterium, C-13 or N-15.

In a further aspect, the present invention is related to a nucleic acid coding for the CD3 kappa peptide, i.e. the CD3 kappa peptide having the amino acid sequence according to SEQ. ID:No. 4, any full-length derivative, any truncated derivative and any modified derivative also referred to herein in their entity as the CD3 kappa peptide or CD3 kappa peptides.

It will be acknowledged by the one skilled in the art that due to the genetic code, it is possible to perceive a nucleic acid sequence coding for the CD3 kappa peptides as disclosed herein. It is obvious that due to the degeneracy of the genetic code, different nucleic acid sequences coding for the same peptide are possible insofar. The preferred nucleic acid sequence for the new open reading frame is the one according to SEQ ID NO:2 and the preferred nucleic acid coding for CD3 kappa having the amino acid sequence according to SEQ ID NO:4, is the nucleic acid sequence according to SEQ ID NO:3.

A further factor which can have an impact on the particular nucleic acid sequence and its design is based on the specific codon usage of the host organism which is used for the expression of the respective nucleic acid sequence. This is also known to the one skilled in the art and can be used for the design of a particular nucleic acid sequence coding for the CD3 kappa peptides as disclosed herein.

The nucleic acids according to the present invention also comprise sequences which are at least partially complementary to such nucleic acid sequences. Preferably, the nucleic acids are homologous to such nucleic acid sequence, whereby the homology is preferably at least 80%, 85%, 90%, 95%, 96%, 97%, 98% or 99%, respectively.

Also, the nucleic acid sequences according to the present invention comprise those which hybridize to any of the nucleic acid sequences disclosed herein. Preferably, the hybridization occurs under conditions of high stringency as, for example, described in Southern, E. M. (1975) J. Mol. Biol. 98, 503-517.

Also, the nucleic acid sequences according to the present invention comprise those which, but for the degeneracy of the genetic code, would hybridize to any of the afore-defined nucleic acid sequences. Preferably the hybridization conditions are conditions of high stringency as, for example a hybridization solution consisting of 1.5×SSPE (0.27 M NaCl, 15 mM sodium.

phosphate (pH 7.7), 1.5 mM EDTA), 0.5% (w/v) non-fat powdered milk; 14), and 1% (w/v) SDS with hybridization carried out at 68° C. for up to 20 h, as described in Khandjian, E. W. (1987) Biotechnology 5, 165-167 or Reed, K. C. and Mann, D. A. (1985) Nucl. Acids Res. 13, 7207-7221.

The nucleic acids according to the present invention such as specifically those disclosed herein may be present in an isolated form, as RNA, as DNA or as hybrids thereof. Preferably, the nucleic acid sequences according to the present invention are contained in a vector. Such a vector is preferably a plasmid vector or a viral vector, however, not limited thereto. A vector as preferably used herein is a nucleic acid sequence which is suitable to express a nucleic acid cloned into it. Preferably such vector comprises a sequence which allows the vector to preferably stably replicate in a host organism and to express the nucleic acid sequence encoded by said vector. Preferably the expression is controlled by a promoter and optionally other expression-regulating factors and sequences, respectively. Vectors are most preferably expression vectors which are known to the one skilled in the art. Depending on the host organism where such vector shall be used and expressed, respectively, the vector can be a mammalian vector, an insect vector, a microbial vector and a viral vector, respectively. This includes also transfection with RNA e.g. of dendritic cells as described in Gilboa E, Vieweg J. Cancer immunotherapy with mRNA-transfected dendritic cells. Immunol Rev. 2004 June; 199:251-63.

Examples of a possible mammalian vector include pCMV4 as described by Andersson, S., Davis, D. L., Dahlback, H., Jornvall, H., Russell, D. W.: Cloning, structure, and expression of the mitochondrial cytochrome P-450 sterol 26-hydroxylase, a bile acid biosynthetic enzyme. J Biol Chem. 1989 May 15; 264(14):8222-9 or an insect vector like a baculovirus which can be either used to transfect insect cell for recombinant protein production or used to transfer genetic material into mammalian cells, as described in Hu Y C. Baculovirus as a highly efficient expression vector in insect and mammalian cells. Acta Pharmacol Sin. 2005 April; 26(4): 405-16 or in Tani H, Limn C K, Yap C C, Onishi M, Nozaki M, Nishimune Y, Okahashi N, Kitagawa Y, Watanabe R, Mochizuki R, Moriishi K, Matsuura Y. In vitro and in vivo gene delivery by recombinant baculoviruses. J Virol. 2003 September; 77(18):9799-808.

Examples of possible microbial vectors are pUC18, pUC19, pBluescript or pBR322 as described in Sambrook, J., Fritsch, E. F., and Maniatis, T. (1989). Molecular Cloning: A Laboratory Manual, Second Edition (Plainview, N.Y.: Cold Spring Harbor Laboratory Press) or in Ausubel, F. M., Brent, R., Kingston, R. E., Moore, D. D., Seidman, J. G., Smith, J. A., and Struhl, K. (1994). Current Protocols in Molecular Biology (New York: Greene Publishing Associates and Wiley-Interscience).

Preferred viral vectors are retroviral vectors like pLN, pLXSN, pLNCX, pLNSX, pLNL6, pLXSHD, pLHDCX or pLXSH as described in Coffin, J. M. & Varmus, H. E., Eds. (1996) Retroviruses (Cold Spring Harbor Laboratory Press, NY), adenoviral vectors like pAdTrack-CMV, pAdTrack or pShuttle-CMV as described in He T C, Zhou S, da Costa L T, Yu J, Kinzler K W, Vogelstein B. A simplified system for generating recombinant adenoviruses. Proc Natl Acad Sci USA. 1998 Mar. 3; 95(5):2509-14 or adeno-associated virus vectors for gene transfer into mammalian cells as described in Zolotukhin S. Production of recombinant adeno-associated virus vectors. Hum Gene Ther. 2005 May; 16(5):551-7.

In a further aspect, the present invention is related to a host cell comprising either a nucleic acid according to the present invention or a vector according to the present invention. Preferably, the host cell is an animal cell and more preferably a mammalian cell. However, the host cell may also be a microbial cell, both a prokaryotic cell and a eukaryotic cell such as a yeast cell or an insect cell.

In case the cell is a mammalian cell and more particularly a human cell, such cell is preferably an isolated human cell. Most preferably the cell is a cell of hematopoetic origin.

It will be appreciated by the one skilled in the art that once such a nucleic acid, vector and host cell, respectively, in accordance with the present invention, is available, the respective peptide can be synthesised using an expression system. Preferably a respective host cell is cultivated in a medium under conditions which allow the production of the peptide encoded by the nucleic acid sequence which is preferably exogenously introduced into said cell. Subsequently, the peptide is harvested, whereby such harvest can be from the culture supernatant or from the cellular cytoplasm upon disrupting the host cell.

Any such vectors, host cells and other elements described herein are as such known to the one skilled in the art and are, for example, described in Sambrook, J., Fritsch, E. F., and Maniatis, T. (1989). Molecular Cloning: A Laboratory Manual, Second Edition (Plainview, N.Y.: Cold Spring Harbor Laboratory Press) or in Ausubel, F. M., Brent, R., Kingston, R. E., Moore, D. D., Seidman, J. G., Smith, J. A., and Struhl, K. (1994). Current Protocols in Molecular Biology (New York: Greene Publishing Associates and Wiley-Interscience) which is incorporated herein by reference.

As disclosed herein, the CD3 kappa peptides improve the surface expression of the T cell receptor, of CD4, CD2, and of some Chemokine and Cytokine-Receptors, more specifically of Cytokine/Chemokine-Receptors which lead to antiapoptotic and/or proliferation inducing effects and have thus an effect which is supportive to the TCR related effects described herein. Most specifically CD3 kappa leads to an up-regulation of CD25, CD116, CD127, CCR3, CCR9 and CXCR1. CD3 kappa also leads to a slight up-regulation of CXCR3 and CXCR4. Based thereon, in principle, any disease involving the T cell receptor and accordingly any disease involving reduced T cell function and/or reduced survival of T-lymphocytes can be treated or prevented by influencing, either directly or indirectly, the CD3 kappa peptide mediated improved surface expression of TCR and of the antiapoptotic and/or proliferation inducing receptors specified herein. Therefore, the diseases for the prevention and/or treatment of which the CD3 kappa peptides and the nucleic acids coding therefor as well as any other of the CD3 kappa peptide related compounds which are described and disclosed herein, can be specifically used are immune-related diseases. Immune-related diseases as preferably used herein are diseases which are characterized by the TCR, the anti-apoptotic and/or proliferation inducing receptors specified herein, and/or the cytokines specified herein which are involved in the pathogenetic mechanism, whereby such pathogenetic mechanism allows that by modifying the surface expression of the T cell receptor to prevent, ameliorate, relieve or cure such disease, either directly or indirectly via the other receptors and cytokines, respectively, specified herein.

To the extent that a disease is characterized by an, in the broader sense, insufficient T cell receptor expression, the CD3 kappa peptides and the nucleic acid coding therefor, can be used for the treatment and prevention, respectively, of such disease. As preferably used herein, the term insufficient T cell receptor expression refers to a level of expression which gives rise to, is linked to or is associated with a pathological condition which is the respective disease, a pre-stage thereof or which increases the susceptibility of a subject for such disease. More specifically, the diseases for the treatment and prevention of which CD3 kappa peptides and the nucleic acids coding therefor, can preferably be used are HIV/Aids, immune defect after treatment with chemotherapy, such as, treatment with a nucleoside-analogue like fludarabine, cytarabine, gemcitabine; an alkylating agent like cyclophosphomide, melphalan, BCNU; an antibody like Alemtuzumab; an anthracycline like doxorubicin, daunorubicin or idarubicine; or radiation; enhancement of the function of ex vivo or in vitro generated T cells for, e.g. adoptive T cell therapy; common variable immunodeficiency, severe combined immunodeficiencies, treatment of cancer, augmentation of cellular immunity and treatment of infections. Most specifically, patients with a lower TCR expression are defined by a difference to the mean value of TCR expression of the healthy subjects plus three times the standard deviation which is statistically significant reduced TCR expression.

Additionally, the diseases may be autoimmune disorders which can be treated via stimulation of regulatory T cells, whereby the autoimmune diseases are particularly those disclosed herein, more specifically those disclosed which can be treated and prevented, respectively, by using the CD3 kappa peptide related compounds. Without wishing to be bound by any theory such kind of diseases can be treated and/or prevented by reducing the effect of the CD3 kappa peptide the abundant titre of which is characteristic for this kind of diseases.

In principle, the treatment and/or prevention of each and any infection is an infectious disease caused or associated with one or several of the viruses and organisms, respectively, recited in table 1. Most preferably CD3 kappa peptides are used as adjuvants for vaccines for the treatment and/or prevention of such diseases or for the treatment and/or prevention of chronic and/or probably lethal forms of such diseases.

TABLE 1

Infectious diseases which can be treated in accordance with the present invention

| | | | | | |
|---|---|---|---|---|---|
| 1. | Human immundefiency virus | - | H10N4 subtype | - | H12N8 subtype |
| | 1-Infection | - | H10N5 subtype | - | H13N2 subtype |
| 2. | Human immundefiency virus | - | H10N7 subtype | - | H13N3 subtype |
| | 2-Infection | - | H10N8 subtype | - | H13N6 subtype |
| 3. | Human immundefiency virus | - | H10N9 subtype | - | H13N7 subtype |
| | 3-Infection | - | H11N1 subtype | - | H14N5 subtype |
| 4. | Human T-cell lymphotropic | - | H11N13 subtype | - | H14N6 subtype |
| | virus | - | H11N2 subtype | - | H15N8 subtype |
| 5. | Hepatitis A Virus-Infection | - | H11N4 subtype | - | H15N9 subtype |
| 6. | Hepatitis B Virus-Infection | - | H11N6 subtype | - | H16N3 subtype |
| 7. | Hepatitis C Virus-Infection | - | H11N8 subtype | - | H1N1 subtype |
| 8. | Hepatitis D Virus-Infection | - | H11N9 subtype | - | H1N2 subtype |
| 9. | Hepatitis E Virus-Infection | - | H12N1 subtype | - | H1N3 subtype |
| 10. | Hepatitis G Virus-Infection | - | H12N4 subtype | - | H1N6 subtype |
| 11. | Influenza A Virus-Infection | - | H12N5 subtype | - | H1N9 subtype |
| - | H2N1 subtype | - | H7N5 subtype | - | SARS coronavirus A022 |
| - | H2N2 subtype | - | H7N7 subtype | - | SARS coronavirus A030 |
| - | H2N3 subtype | - | H7N8 subtype | - | SARS coronavirus A031 |
| - | H2N5 subtype | - | H8N4 subtype | - | SARS coronavirus AS |
| - | H2N7 subtype | - | H8N5 subtype | - | SARS coronavirus B012 |
| - | H2N8 subtype | - | H9N1 subtype | - | SARS coronavirus B024 |
| - | H2N9 subtype | - | H9N2 subtype | - | SARS coronavirus B029 |
| - | H3N1 subtype | - | H9N3 subtype | - | SARS coronavirus B033 |
| - | H3N2 subtype | - | H9N5 subtype | - | SARS coronavirus B039 |
| - | H3N3 subtype | - | H9N6 subtype | - | SARS coronavirus B040 |
| - | H3N4 subtype | - | H9N7 subtype | - | SARS coronavirus BJ01 |
| - | H3N5 subtype | - | H9N8 subtype | - | SARS coronavirus BJ02 |
| - | H3N6 subtype | - | H9N9 subtype | - | SARS coronavirus BJ03 |
| - | H3N8 subtype | 12. | Influenza B Virus-Infection | - | SARS coronavirus BJ04 |
| - | H4N1 subtype | 13. | Influenza C Virus-Infection | - | SARS coronavirus BJ2232 |
| - | H4N2 subtype | 14. | Human astrovirus | - | SARS coronavirus BJ302 |
| - | H4N3 subtype | 15. | Human norovirus | - | SARS coronavirus C013 |
| - | H4N4 subtype | 16. | Human calicivirus | - | SARS coronavirus C014 |
| - | H4N5 subtype | 17. | Dengue virus group | - | SARS coronavirus C017 |
| - | H4N6 subtype | 18. | Japanese encephalitis virus | - | SARS coronavirus C018 |
| - | H4N8 subtype | | group | - | SARS coronavirus C019 |
| - | H4N9 subtype | 19. | Kokobera virus group | - | SARS coronavirus C025 |
| - | H5N1 subtype | 20. | Modoc virus group | - | SARS coronavirus C028 |
| - | H5N2 subtype | 21. | mosquito-borne viruses | - | SARS coronavirus C029 |
| - | H5N3 subtype | 22. | Ntaya virus group | - | SARS Coronavirus |

TABLE 1-continued

Infectious diseases which can be treated in accordance with the present invention

- H5N4 subtype
- H5N6 subtype
- H5N7 subtype
- H5N8 subtype
- H5N9 subtype
- H6N1 subtype
- H6N2 subtype
- H6N4 subtype
- H6N5 subtype
- H6N6 subtype
- H6N7 subtype
- H6N8 subtype
- H6N9 subtype
- H7N1 subtype
- H7N2 subtype
- H7N3 subtype
- SARS coronavirus cw037
- SARS coronavirus cw049
- SARS coronavirus FRA
- SARS coronavirus Frankfurt 1
- SARS coronavirus GD01
- SARS coronavirus GD03T0013
- SARS coronavirus GD322
- SARS coronavirus GD69
- SARS coronavirus GZ-A
- SARS coronavirus GZ-B
- SARS coronavirus GZ-C
- SARS coronavirus GZ-D
- SARS coronavirus GZ02
- SARS coronavirus GZ0401
- SARS coronavirus GZ0402
- SARS coronavirus GZ0403
- SARS coronavirus GZ43
- SARS coronavirus GZ50
- SARS coronavirus GZ60
- SARS coronavirus HB
- SARS coronavirus HC/SZ/61/03
- SARS coronavirus HGZ8L1-A
- SARS coronavirus HGZ8L1-B
- SARS coronavirus HGZ8L2
- SARS coronavirus HHS-2004
- SARS coronavirus HKU-36871
- SARS coronavirus HKU-39849
- SARS coronavirus HKU-65806
- SARS coronavirus HKU-66078
- SARS coronavirus Hong Kong/03/2003
- SARS coronavirus TW
- SARS coronavirus TW-GD1
- SARS coronavirus TW-GD2
- SARS coronavirus TW-GD3
- SARS coronavirus TW-GD4
- SARS coronavirus TW-GD5
- SARS coronavirus TW-HP1
- SARS coronavirus TW-HP2
- SARS coronavirus TW-HP3
- SARS coronavirus TW-HP4
- SARS coronavirus TW-JC2
- SARS coronavirus TW-KC1
- SARS coronavirus TW-KC3
- SARS coronavirus TW-PH1
- SARS coronavirus TW-PH2
- SARS coronavirus TW-YM1
- SARS coronavirus TW-YM2
- SARS coronavirus TW-YM3
- SARS coronavirus TW-YM4
- SARS coronavirus TW1

23. Rio Bravo virus group
24. Seaborne tick-borne virus group
25. Spondweni virus group
26. tick-borne encephalitis virus group
27. Yaounde virus
28. Yellow fever virus group
29. GB virus A
30. GBV-C/HGV group
31. Hepatitis GB virus B
32. Marmoset hepatitis GB virus A
33. Human coronavirus
    - SARS coronavirus A001
    - SARS coronavirus A013
    - SARS coronavirus A021
    - SARS coronavirus HPZ-2003
    - SARS coronavirus HSR 1
    - SARS coronavirus HSZ-A
    - SARS coronavirus HSZ-Bb
    - SARS coronavirus HSZ-Bc
    - SARS coronavirus HSZ-Cb
    - SARS coronavirus HSZ-Cc
    - SARS coronavirus HSZ2-A
    - SARS coronavirus HZS2-Bb
    - SARS coronavirus HZS2-C
    - SARS coronavirus HZS2-D
    - SARS coronavirus HZS2-E
    - SARS coronavirus HZS2-Fb
    - SARS coronavirus HZS2-Fc
    - SARS coronavirus JMD
    - SARS coronavirus LC1
    - SARS coronavirus LC2
    - SARS coronavirus LC3
    - SARS coronavirus LC4
    - SARS coronavirus LC5
    - SARS coronavirus LLJ-2004
    - SARS coronavirus NS-1
    - SARS coronavirus PC4-115
    - SARS coronavirus PC4-127
    - SARS coronavirus PC4-13
    - SARS coronavirus PC4-136
    - SARS coronavirus PC4-137
    - SARS coronavirus PC4-145
    - SARS coronavirus PC4-199
    - SARS coronavirus PC4-205
    - SARS coronavirus PC4-227
    - SARS coronavirus PC4-241
    - SARS coronavirus PUMC01
    - SARS coronavirus PUMC02
    - SARS coronavirus PUMC03
    - SARS coronavirus sf098
    - SARS coronavirus sf099
    - SARS coronavirus ShanghaiQXC1
    - SARS coronavirus ShanghaiQXC2
    - SARS coronavirus WHU
    - SARS coronavirus xw002
    - SARS coronavirus ZJ01
    - SARS coronavirus ZJ02
    - SARS coronavirus ZJ0301
    - SARS coronavirus ZMY 1
    - SARS coronavirus ZS-A
    - SARS coronavirus ZS-B
    - SARS coronavirus ZS-C
34. Theiler's encephalomyelitis virus
35. Human enterovirus A
36. Enterovirus 5666/sin/002209
37. Enterovirus 5865/sin/000009
38. Human coxsackievirus A10
39. Human coxsackievirus A12
40. Human coxsackievirus A14
41. Human coxsackievirus A16
42. Human coxsackievirus A2
43. Human coxsackievirus A3

CDC#200301157
- SARS coronavirus civet007
- SARS coronavirus civet010
- SARS coronavirus civet014
- SARS coronavirus civet019
- SARS coronavirus civet020
- SARS coronavirus CUHK-AG01
- SARS coronavirus CUHK-AG02
- SARS coronavirus CUHK-AG03
- SARS coronavirus CUHK-L2
- SARS coronavirus CUHK-Su10
- SARS coronavirus CUHK-W1
- SARS coronavirus Shanhgai LY
- SARS coronavirus Sin0409
- SARS coronavirus Sin2500
- SARS coronavirus Sin2677
- SARS coronavirus Sin2679
- SARS coronavirus Sin2748
- SARS coronavirus Sin2774
- SARS coronavirus Sin3408
- SARS coronavirus Sin3408L
- SARS coronavirus Sin3725V
- SARS coronavirus Sin3765V
- SARS coronavirus Sin842
- SARS coronavirus Sin845
- SARS coronavirus Sin846
- SARS coronavirus Sin847
- SARS coronavirus Sin848
- SARS coronavirus Sin849
- SARS coronavirus Sin850
- SARS coronavirus Sin852
- SARS coronavirus Sin__WNV
- SARS coronavirus Sino1-11
- SARS coronavirus Sino3-11
- SARS coronavirus SinP1
- SARS coronavirus SinP2
- SARS coronavirus SinP3
- SARS coronavirus SinP4
- SARS coronavirus SinP5
- SARS coronavirus SoD
- SARS coronavirus SZ1
- SARS coronavirus SZ13
- SARS coronavirus SZ16
- SARS coronavirus SZ3
- SARS coronavirus Taiwan
- SARS coronavirus Taiwan JC-2003
- SARS coronavirus Taiwan TC1
- SARS coronavirus Taiwan TC2
- SARS coronavirus Taiwan TC3
- SARS coronavirus TJF
- SARS coronavirus Tor2

65. Human coxsackievirus B6
66. Human echovirus 1
67. Human echovirus 11
68. Human echovirus 12
69. Human echovirus 13
70. Human echovirus 14
71. Human echovirus 15
72. Human echovirus 16
73. Human echovirus 17
74. Human echovirus 18
75. Human echovirus 19
76. Human echovirus 2
77. Human echovirus 20
78. Human echovirus 21
79. Human echovirus 24
80. Human echovirus 25
81. Human echovirus 26
82. Human echovirus 27
83. Human echovirus 29
84. Human echovirus 3

TABLE 1-continued

| Infectious diseases which can be treated in accordance with the present invention |
|---|
| - SARS coronavirus TW10 |
| - SARS coronavirus TW11 |
| - SARS coronavirus TW2 |
| - SARS coronavirus TW3 |
| - SARS coronavirus TW4 |
| - SARS coronavirus TW5 |
| - SARS coronavirus TW6 |
| - SARS coronavirus TW7 |
| - SARS coronavirus TW8 |
| - SARS coronavirus TW9 |
| - SARS coronavirus TWC |
| - SARS coronavirus TWC2 |
| - SARS coronavirus TWC3 |
| - SARS coronavirus TWH |
| - SARS coronavirus TWJ |
| - SARS coronavirus TWK |
| - SARS coronavirus TWS |
| - SARS coronavirus TWY |
| - SARS coronavirus Urbani |
| - SARS coronavirus Vietnam |
| - SARS coronavirus WH20 |
| 44. Human coxsackievirus A4 |
| 45. Human coxsackievirus A5 |
| 46. Human coxsackievirus A6 |
| 47. Human coxsackievirus A7 |
| 48. Human coxsackievirus A8 |
| 49. Human enterovirus 71 |
| 50. Human enterovirus 76 |
| 51. Human enterovirus 89 |
| 52. Human enterovirus 90 |
| 53. Human enterovirus 91 |
| 54. Human enterovirus B |
| 55. Enterovirus 69 |
| 56. Enterovirus 74 |
| 57. Enterovirus CA55-1988 |
| 58. Enterovirus Yanbian 96-83csf |
| 59. Human coxsackievirus A9 |
| 60. Human coxsackievirus B1 |
| 61. Human coxsackievirus B2 |
| 62. Human coxsackievirus B3 |
| 63. Human coxsackievirus B4 |
| 64. Human coxsackievirus B5 |
| 85. Human echovirus 30 |
| 86. Human echovirus 31 |
| 87. Human echovirus 32 |
| 88. Human echovirus 33 |
| 89. Human echovirus 4 |
| 90. Human echovirus 5 |
| 91. Human echovirus 6 |
| 92. Human echovirus 7 |
| 93. Human echovirus 8 |
| 94. Human echovirus 9 |
| 95. Human enterovirus 69 |
| 96. Human enterovirus 73 |
| 97. Human enterovirus 74 |
| 98. Human enterovirus 75 |
| 99. Human enterovirus 77 |
| 100. Human enterovirus 78 |
| 101. Swine vesicular disease virus |
| 102. Human enterovirus C |
| 103. Human coxsackievirus A1 |
| 104. Human coxsackievirus A11 |
| 105. Human coxsackievirus A13 |
| 106. Human coxsackievirus A15 |
| 107. Human coxsackievirus A11 |
| 108. Human coxsackievirus A18 |
| 109. Human coxsackievirus A19 |
| 110. Human coxsackievirus A20 |
| 111. Human coxsackievirus A21 |
| 112. Human coxsackievirus A22 |
| 113. Human coxsackievirus A24 |
| 114. Human enterovirus D |
| 115. Human enterovirus 68 |
| 116. Human enterovirus 70 |
| 117. Poliovirus |
| 118. Human poliovirus 1 |
| 119. Human poliovirus 2 |
| 120. Human poliovirus 3 |
| 121. Wild poliovirus type 3 |
| 122. Human parechovirus 1 |
| 123. Human parechovirus 2 |
| 124. Human parechovirus 3 |
| 125. Human rhinovirus A |
| 126. Human rhinovirus 10 |
| 127. Human rhinovirus 100 |
| 128. Human rhinovirus 11 |
| 129. Human rhinovirus 12 |
| 130. Human rhinovirus 13 |
| 131. Human rhinovirus 15 |
| 132. Human rhinovirus 16 |
| 133. Human rhinovirus 18 |
| 134. Human rhinovirus 19 |
| 135. Human rhinovirus 1A |
| 136. Human rhinovirus 1B |
| 137. Human rhinovirus 2 |
| 138. Human rhinovirus 20 |
| 139. Human rhinovirus 21 |
| 140. Human rhinovirus 22 |
| 141. Human rhinovirus 23 |
| 142. Human rhinovirus 24 |
| 143. Human rhinovirus 25 |
| 144. Human rhinovirus 28 |
| 145. Human rhinovirus 29 |
| 146. Human rhinovirus 30 |
| 147. Human rhinovirus 31 |
| 148. Human rhinovirus 32 |
| 149. Human rhinovirus 33 |
| 150. Human rhinovirus 34 |
| 151. Human rhinovirus 36 |
| 152. Human rhinovirus 38 |
| 153. Human rhinovirus 39 |
| 154. Human rhinovirus 40 |
| 155. Human rhinovirus 41 |
| 156. Human rhinovirus 43 |
| 157. Human rhinovirus 44 |
| 158. Human rhinovirus 45 |
| 159. Human rhinovirus 46 |
| 160. Human rhinovirus 47 |
| 161. Human rhinovirus 49 |
| 162. Human rhinovirus 50 |
| 163. Human rhinovirus 51 |
| 164. Human rhinovirus 53 |
| 165. Human rhinovirus 54 |
| 166. Human rhinovirus 55 |
| 167. Human rhinovirus 56 |
| 168. Human rhinovirus 57 |
| 169. Human rhinovirus 58 |
| 170. Human rhinovirus 59 |
| 171. Human rhinovirus 60 |
| 172. Human rhinovirus 61 |
| 173. Human rhinovirus 62 |
| 174. Human rhinovirus 63 |
| 175. Human rhinovirus 64 |
| 176. Human rhinovirus 65 |
| 177. Human rhinovirus 66 |
| 178. Human rhinovirus 67 |
| 179. Human rhinovirus 68 |
| 180. Human rhinovirus 7 |
| 181. Human rhinovirus 71 |
| 182. Human rhinovirus 73 |
| 183. Human rhinovirus 74 |
| 184. Human rhinovirus 75 |
| 185. Human rhinovirus 76 |
| 186. Human rhinovirus 77 |
| 187. Human rhinovirus 78 |
| 188. Human rhinovirus 8 |
| 189. Human rhinovirus 80 |
| 190. Human rhinovirus 81 |
| 191. Human rhinovirus 82 |
| 192. Human rhinovirus 85 |
| 193. Human rhinovirus 88 |
| 194. Human rhinovirus 89 |
| 195. Human rhinovirus 9 |
| 196. Human rhinovirus 90 |
| 197. Human rhinovirus 94 |
| 198. Human rhinovirus 95 |
| 199. Human rhinovirus 96 |
| 200. Human rhinovirus 98 |
| 201. Human rhinovirus B |
| 202. Human rhinovirus 14 |
| 203. Human rhinovirus 17 |
| 204. Human rhinovirus 26 |
| 205. Human rhinovirus 27 |
| 206. Human rhinovirus 3 |
| 207. Human rhinovirus 35 |
| 208. Human rhinovirus 37 |
| 209. Human rhinovirus 4 |
| 210. Human rhinovirus 42 |
| 211. Human rhinovirus 48 |
| 212. Human rhinovirus 5 |
| 213. Human rhinovirus 52 |
| 214. Human rhinovirus 6 |
| 215. Human rhinovirus 69 |
| 216. Human rhinovirus 70 |
| 217. Human rhinovirus 72 |
| 218. Human rhinovirus 79 |
| 219. Human rhinovirus 83 |
| 220. Human rhinovirus 84 |
| 221. Human rhinovirus 86 |
| 222. Human rhinovirus 91 |
| 223. Human rhinovirus 92 |
| 224. Human rhinovirus 93 |
| 225. Human rhinovirus 97 |
| 226. Human rhinovirus 99 |
| 227. Human rhinovirus 001 Finland Nov1995 |
| 228. Human rhinovirus 166 Finland Sep1995 |
| 229. Human rhinovirus 253 Finland Sep1994 |
| 230. Human rhinovirus 263 Berlin 2004 |
| 231. Human rhinovirus 317 Finland Aug1996 |
| 232. Human rhinovirus 425 Finland Dec1995 |
| 233. Human rhinovirus 851 Finland Sep1996 |
| 234. Human rhinovirus 864 Finland Sep1996 |
| 248. Human herpesvirus 7-Infection |
| 249. Human herpesvirus 8 (Kaposi's sarcoma-associated herpesvirus)-Infection |
| 250. Human papillomavirus-10 |
| 251. Human papillomavirus type 10 |
| 252. Human papillomavirus type 28 |
| 253. Human papillomavirus type 29 |
| 254. Human papillomavirus type 3 |
| 255. Human papillomavirus type 77 |
| 256. Human papillomavirus type 94 |
| 257. Human papillomavirus-16 |
| 258. Human papillomavirus type 16 |
| 259. Human papillomavirus type 31 |
| 283. Human papillomavirus type 26 |
| 284. Human papillomavirus type 51 |
| 285. Human papillomavirus type 69 |
| 286. Human papillomavirus type 82 |
| 287. Human papillomavirus-32 |
| 288. Human papillomavirus type 32 |
| 289. Human papillomavirus type 42 |
| 290. Human papillomavirus-34 |
| 291. Human papillomavirus type 34 |
| 292. Human papillomavirus type 73 |
| 293. Human papillomavirus-53 |
| 294. Human papillomavirus type 30 |
| 295. Human papillomavirus type 53 |
| 296. Human papillomavirus type 56 |

TABLE 1-continued

Infectious diseases which can be treated in accordance with the present invention 235. Human rhinovirus 928 Finland May1995
236. Human rhinovirus strain Hanks
237. Untyped human rhinovirus OK88-8162
238. Rubella virus
239.
240. Human respiratory syncytial virus A
241. Human respiratory syncytial virus B
242. Human herpesvirus 1 (Herpes simplex)-Infection
243. Human herpesvirus 2-Infection
244. Human herpesvirus 3 (Varicella-zoster virus)-Infection
245. Human herpesvirus 4 (Epstein-Barr virus)-Infection
246. Human herpesvirus 5 (Cytomegalovirus)-Infection
247. Human herpesvirus 6-Infection
260. Human papillomavirus type 33
261. Human papillomavirus type 35
262. Human papillomavirus type 35H
263. Human papillomavirus type 52
264. Human papillomavirus type 58
265. Human papillomavirus type 67
266. Human papillomavirus-18
267. Human papillomavirus-cand85
268. Human papillomavirus type 18
269. Human papillomavirus type 39
270. Human papillomavirus type 45
271. Human papillomavirus type 59
272. Human papillomavirus type 68
273. Human papillomavirus type 70
274. Human papillomavirus-2
275. Human papillomavirus type 2
276. Human papillomavirus type 27
277. Human papillomavirus type 27b
278. Human papillomavirus type 2a
279. Human papillomavirus type 2c
280. Human papillomavirus type 57
281. Human papillomavirus type 57b
282. Human papillomavirus-26
297. Human papillomavirus type 66
298. Human papillomavirus-54
299. Human papillomavirus-6
300. Human papillomavirus type 11
301. Human papillomavirus type 13
302. Human papillomavirus type 44
303. Human papillomavirus type 55
304. Human papillomavirus type 6
305. Human papillomavirus type 6a
306. Human papillomavirus type 6b
307. Human papillomavirus type 6c
308. Human papillomavirus type 6e
309. Human papillomavirus type 6vc
310. Human papillomavirus type 74
311. Pygmy chimpanzee papillomavirus type 1
312. Human papillomavirus - 61
313. Human papillomavirus - 72
314. Human papillomavirus - 81
315. Human papillomavirus - 83
316. Human papillomavirus-cand62
317. Human papillomavirus-cand86
318. Human papillomavirus-cand87
319. Human papillomavirus-cand89
320. Human papillomavirus type 61
321. Human papillomavirus type 84
322. Human papillomavirus-7
323. Human papillomavirus-cand91
324. Human papillomavirus type 40
325. Human papillomavirus type 43
326. Human papillomavirus type 7
327. Human papillomavirus-71
328. Human papillomavirus type 71
329. Human papillomavirus-cand90
330. Human papillomavirus-49
331. Human papillomavirus type 49
332. Human papillomavirus type 75
333. Human papillomavirus type 76
334. Human papillomavirus-5
335. Human papillomavirus type 12
336. Human papillomavirus type 14
337. Human papillomavirus type 14D
338. Human papillomavirus type 19
339. Human papillomavirus type 20
340. Human papillomavirus type 21
341. Human papillomavirus type 25
342. Human papillomavirus type 36
343. Human papillomavirus type 47
344. Human papillomavirus type 5
345. Human papillomavirus type 5b
346. Human papillomavirus type 8
347. Human papillomavirus type 93
348. Human papillomavirus-9
349. Human papillomavirus type 15
350. Human papillomavirus type 17
351. Human papillomavirus type 22
352. Human papillomavirus type 23
353. Human papillomavirus type 37
354. Human papillomavirus type 38
355. Human papillomavirus type 38b
356. Human papillomavirus type 80
357. Human papillomavirus type 9
358. Human papillomavirus-cand92
359. Human papillomavirus type 92
360. Human papillomavirus-cand96
361. Human papillomavirus type 96
362. Human papillomavirus-4
363. Human papillomavirus type 4
364. Human papillomavirus type 65
365. Human papillomavirus type 95
366. Human papillomavirus-48
367. Human papillomavirus type 48
368. Human papillomavirus-50
369. Human papillomavirus type 50
370. Human papillomavirus-60
371. Human papillomavirus type 60
372. Human papillomavirus-1
373. Human papillomavirus type 1a
374. Human papillomavirus-41
375. Human papillomavirus type 41
376. Human papillomavirus-63
377. Human papillomavirus type 63
378. Human papillomavirus HANOA464
379. Human papillomavirus RTRX7
380. Human papillomavirus type 24
381. Human papillomavirus type 64
382. Human papillomavirus type JC9710
383. Human papillomavirus type JC9813
384. Human papillomavirus type JEB2
385. Human papillomavirus type me180
386. Human papillomavirus type Xc
387. Human papillomavirus type Xd
388. Human papillomavirus type Xf
389. Human papillomavirus type Xg
390. Human papillomavirus type Xh
391. BK polyomavirus
392. JC polyomavirus
393. Cowpox virus
394. Monkeypox virus
395. Vaccinia virus
396. Variola major virus
397. Variola minor virus
398. Human orf virus
399. Pseudocowpox virus
400. Mammalian orthoreovirus 1
401. Mammalian orthoreovirus 2
402. Mammalian orthoreovirus 3
403. Mammalian orthoreovirus 4 Ndelle
404. SARS orthoreovirus GD-2003
405. Human rotavirus A
406. Human rotavirus B
407. Human rotavirus C
408. Human rotavirus ADRV-N
409. Human parvovirus B19
410. Adeno-associated virus
411. Adeno-associated virus - 1
412. Adeno-associated virus 6
413. Adeno-associated virus-2
414. Adeno-associated virus 2H
415. Adeno-associated virus-3
416. Adeno-associated virus 3B
417. Adeno-associated virus-4
418. Adeno-associated virus-5
419. Adeno-associated virus-7
420. Adeno-associated virus-8
421. Adeno-associated virus 10
454. Four Corners hantavirus
455. Hantaan virus
456. Hu39694 virus
457. Isla Vista virus
458. Khabarovsk virus
459. Laguna Negra virus
460. Limestone Canyon virus
461. Muleshoe virus
462. New York virus
493. Oriboca virus
494. Oropouche virus
495. Sathuperi virus
496. Shamonda virus
497. Shuni virus
498. Simbu virus
499. Wyeomyia virus
500. Punta Toro virus
501. Rift Valley fever virus TABLE 1-continued Infectious diseases which can be treated in accordance with the present invention 422. Adeno-associated virus 11
423. Adeno-associated virus 12
424. Adeno-associated virus 9
425. Human erythrovirus V9
426. Human erythrovirus VX
427. Simian parvovirus
428. Human parvovirus 4
429. Allpahuayo virus
430. Amapari virus
431. Bear Canyon virus
432. Cupixi virus
433. Flexal virus
434. Guanarito virus
435. Junin virus
436. Latino virus
437. Machupo virus
438. Oliveros virus
439. Parana virus
440. Pichinde virus
441. Pirital virus
442. Sabia virus
443. Tacaribe virus
444. Tamiami virus
445. Whitewater Arroyo virus
446. Lassa virus
447. Amur virus
448. Andes virus
449. Bayou virus
450. Black Creek Canal virus
451. Cano Delgadito virus
452. Dobrava virus
453. El Moro Canyon hantavirus
463. Prairie vole hantavirus
464. Prospect Hill virus
465. Puumala virus
466. Reithrodontomys mexicanus hantavirus
467. Rio Mamore virus
468. Sapporo rat virus
469. Seoul virus
470. Sin Nombre virus
471. Taimyr hantavirus
472. Thailand virus
473. Thottapalayam virus
474. Topografov virus
475. Tula virus
476. Vladivostok virus
477. Crimean-Congo hemorrhagic fever virus
478. Dera Ghazi Khan virus
479. Dugbe virus
480. Hughes virus
481. Qalyub virus
482. Sakhalin virus
483. Thiafora virus
484. Akabane virus
485. Bunyamwera virus
486. California encephalitis virus
487. Caraparu virus
488. Kairi virus
489. Madrid virus
490. Main Drain virus
491. Manzanilla virus
492. Marituba virus
502. Sandfly fever Naples virus
503. Uukuniemi virus
504. Phlebovirus sp.
505. Bornavirus
506. Cote d'Ivoire ebolavirus
507. Ebola virus
508. Reston ebolavirus
509. Sudan ebolavirus
510. Zaire ebolavirus
511. Marburgvirus
512. Avulavirus
513. Henipavirus
514. Morbillivirus
515. Respirovirus
516. Rubulavirus
517. Human parainfluenza virus 1
518. Human parainfluenza virus 3
519. Human parainfluenza virus 2
520. Human parainfluenza virus 4
521. Human parainfluenza virus 4a
522. Human parainfluenza virus 4b
523. Mapuera virus
524. Mumps virus
525. Human metapneumovirus
526. Rabies virus
527. Hirame rhabdovirus
528. Infectious hematopoietic necrosis virus
529. Viral hemorrhagic septicemia virus
530. Sendai virus
531. Human adenovirus A-Infection
532. Human adenovirus type 12-Infection
533. Human adenovirus type 18-Infection
534. Human adenovirus type 31-Infection
535. Simian adenovirus type 10-Infection
536. Simian adenovirus type 11-Infection
537. Simian adenovirus type 14-Infection
538. Simian adenovirus type 2-Infection
539. Simian adenovirus type 4-Infection
540. Simian adenovirus type 6-Infection
541. Simian adenovirus type 9-Infection
542. Human adenovirus B-Infection
543. Human adenovirus 3 + 7-Infection
544. Human adenovirus type 11-Infection
545. Human adenovirus type 11a-Infection
546. Human adenovirus type 11p-Infection
547. Human adenovirus type 14-Infection
548. Human adenovirus type 16-Infection
549. Human adenovirus type 21-Infection
550. Human adenovirus type 3-Infection
551. Human adenovirus type 34-Infection
552. Human adenovirus type 34a-Infection
553. Human adenovirus type 35-Infection
554. Human adenovirus type 35 + 11-Infection
555. Human adenovirus type 35p-Infection
556. Human adenovirus type 50-Infection
557. Human adenovirus type 50 prototype strain Wan-Infection
558. Human adenovirus type 7-Infection
559. Human adenovirus type 7a-Infection
560. Human adenovirus type 7d-Infection
561. Human adenovirus type 7d2-Infection
562. Human adenovirus type 7l-Infection
563. Human adenovirus type 7p-Infection
564. Simian adenovirus 21-Infection
565. Human adenovirus C-Infection
566. Human adenovirus type 1-Infection
567. Human adenovirus type 2-Infection
568. Human adenovirus type 5-Infection
569. Human adenovirus type 6-Infection
570. Simian adenovirus type 13-Infection
571. Human adenovirus D-Infection
572. Human adenovirus 19a-Infection
573. Human adenovirus 19p-Infection
574. Human adenovirus 37-Infection
575. Human adenovirus type 10-Infection
576. Human adenovirus type 13-Infection
577. Human adenovirus type 15-Infection
578. Human adenovirus type 15/H9-Infection
579. Human adenovirus type 17-Infection
580. Human adenovirus type 19-Infection
581. Human adenovirus type 19a-Infection
582. Human adenovirus type 19p-Infection
583. Human adenovirus type 20-Infection
584. Human adenovirus type 22-Infection
585. Human adenovirus type 23-Infection
586. Human adenovirus type 24-Infection
587. Human adenovirus type 25-Infection
588. Human adenovirus type 26-Infection
589. Human adenovirus type 27-Infection
590. Human adenovirus type 28-Infection
591. Human adenovirus type 29-Infection
592. Human adenovirus type 30-Infection
593. Human adenovirus type 32-Infection
594. Human adenovirus type 33-Infection
595. Human adenovirus type 36-Infection
614. Simian adenovirus 22-Infection
615. Simian adenovirus 23-Infection
641. *Listeria ivanovii* subsp. *ivanovii*
642. *Listeria ivanovii* subsp. *londoniensis*

TABLE 1-continued

Infectious diseases which can be treated in accordance with the present invention 596. Human adenovirus type 37-Infection
597. Human adenovirus type 38-Infection
598. Human adenovirus type 39-Infection
599. Human adenovirus type 42-Infection
600. Human adenovirus type 43-Infection
601. Human adenovirus type 44-Infection
602. Human adenovirus type 45-Infection
603. Human adenovirus type 46-Infection
604. Human adenovirus type 47-Infection
605. Human adenovirus type 48-Infection
606. Human adenovirus type 49-Infection
607. Human adenovirus type 51-Infection
608. Human adenovirus type 8-Infection
609. Human adenovirus type 8E-Infection
610. Human adenovirus type 9-Infection
611. Human adenovirus E-Infection
612. Human adenovirus type 4-Infection
613. Human adenovirus type 4a-Infection
616. Simian adenovirus 24-Infection
617. Simian adenovirus 25-Infection
618. Human adenovirus F-Infection
619. Human adenovirus type 40-Infection
620. Human adenovirus type 41-Infection
621. Simian adenovirus type 19-Infection
622. *Mycobacterium africanum*
623. *Mycobacterium bovis*
624. *Mycobacterium canettii*
625. *Mycobacterium microti*
626. *Mycobacterium pinnipedii*
627. *Mycobacterium tuberculosis*
628. *Mycobacterium leprae*
629. *Pneumocystis carinii f.* sp. *macaca*
630. *Pneumocystis carinii f.* sp. *muris*
631. *Pneumocystis carinii f.* sp. *mustelae*
632. *Pneumocystis carinii f.* sp. *oryctolagi*
633. *Pneumocystis carinii f.* sp. *ratti*
634. *Pneumocystis carinii f.* sp. *rattus-quarti*
635. *Pneumocystis carinii f.* sp. *rattus-secundi*
636. *Pneumocystis carinii f.* sp. *rattus-tertii*
637. *Pneumocystis carinii f.* sp. *Suis*
638. *Listeria grayi*
639. *Listeria innocua*
640. *Listeria ivanovii*
643. *Listeria monocytogenes*
644. *Listeria seeligeri*
645. *Listeria welshimeri*
646. *Bacillus anthracis*
647. *Bacillus cereus*
648. *Yersinia pestis*
649. *Mycoplasma adleri*
650. *Mycoplasma agalactiae*
651. *Mycoplasma agassizii*
652. *Mycoplasma alkalescens*
653. *Mycoplasma alligatoris*
654. *Mycoplasma alvi*
655. *Mycoplasma amphoriforme*
656. *Mycoplasma anatis*
657. *Mycoplasma anseris*
658. *Mycoplasma arginini*
659. *Mycoplasma arthritidis*
660. *Mycoplasma auris*
661. *Mycoplasma* BHJA
662. *Mycoplasma bovigenitalium*
663. *Mycoplasma bovirhinis*
664. *Mycoplasma bovis*
665. *Mycoplasma bovoculi*
666. *Mycoplasma buccale*
667. *Mycoplasma buteonis*
668. *Mycoplasma californicum*
669. *Mycoplasma canadense*
670. *Mycoplasma canis*
671. *Mycoplasma capricolum*
672. *Mycoplasma capricolum* subsp. *capricolum*
673. *Mycoplasma capricolum* subsp. *capripneumoniae*
674. *Mycoplasma caviae*
675. *Mycoplasma cavipharyngis*
676. *Mycoplasma citelli*
677. *Mycoplasma cloacale*
678. *Mycoplasma coccoides*
679. *Mycoplasma collis*
680. *Mycoplasma columbinasale*
681. *Mycoplasma columbinum*
682. *Mycoplasma columborale*
683. *Mycoplasma conjunctivae*
684. *Mycoplasma corogypsi*
685. *Mycoplasma cottewii*
686. *Mycoplasma cricetuli*
687. *Mycoplasma crocodyli*
688. *Mycoplasma cynos*
689. *Mycoplasma dispar*
690. *Mycoplasma edwardii*
691. *Mycoplasma elephantis*
692. *Mycoplasma equigenitalium*
693. *Mycoplasma equirhinis*
694. *Mycoplasma falconis*
695. *Mycoplasma fastidiosum*
696. *Mycoplasma faucium*
697. *Mycoplasma felifaucium*
698. *Mycoplasma feliminutum*
699. *Mycoplasma felis*
700. *Mycoplasma fermentans*
701. *Mycoplasma incognitus*
702. *Mycoplasma flocculare*
703. *Mycoplasma gallinaceum*
704. *Mycoplasma gallinarum*
705. *Mycoplasma gallisepticum*
706. *Mycoplasma gallopavonis*
707. *Mycoplasma gateae*
708. *Mycoplasma genitalium*
709. *Mycoplasma glycophilum*
710. *Mycoplasma gypis*
711. *Mycoplasma haemocanis*
712. *Mycoplasma haemofelis*
713. *Mycoplasma haemomuris*
714. *Mycoplasma hominis*
715. *Mycoplasma hyopharyngis*
716. *Mycoplasma hyopneumoniae*
717. *Mycoplasma hyorhinis*
718. *Mycoplasma hyosynoviae*
719. *Mycoplasma iguanae*
720. *Mycoplasma imitans*
721. *Mycoplasma indiense*
722. *Mycoplasma iners*
723. *Mycoplasma iowae*
724. *Mycoplasma lagogenitalium*
725. *Mycoplasma leonicaptivi*
726. *Mycoplasma leopharyngis*
727. *Mycoplasma lipofaciens*
728. *Mycoplasma lipophilum*
729. *Mycoplasma maculosum*
730. *Mycoplasma meleagridis*
731. *Mycoplasma microti*
732. *Mycoplasma moatsii*
733. *Mycoplasma mobile*
734. *Mycoplasma molare*
735. *Mycoplasma monodon*
736. *Mycoplasma muris*
737. *Mycoplasma mustelae*
738. *Mycoplasma mycoides*
739. *Mycoplasma neurolyticum*
740. *Mycoplasma opalescens*
741. *Mycoplasma orale*
742. *Mycoplasma ovipneumoniae*
743. *Mycoplasma ovis*
744. *Mycoplasma oxoniensis*
745. *Mycoplasma penetrans*
746. *Mycoplasma phocicerebrale*
747. *Mycoplasma phocidae*
748. *Mycoplasma phocirhinis*
749. *Mycoplasma pirum*
750. *Mycoplasma pneumoniae*
751. *Mycoplasma pneumophila*
752. *Mycoplasma primatum*
753. *Mycoplasma pullorum*
754. *Mycoplasma pulmonis*
755. *Mycoplasma putrefaciens*
756. *Mycoplasma salivarium*
757. *Mycoplasma simbae*
758. *Mycoplasma spermatophilum*
759. *Mycoplasma spheniscі*
760. *Mycoplasma spumans*
761. *Mycoplasma sturni*
762. *Mycoplasma sualvi*
763. *Mycoplasma subdolum*
764. *Mycoplasma suis*
765. *Mycoplasma synoviae*
766. *Mycoplasma testudineum*
767. *Mycoplasma testudinis*
768. *Mycoplasma timone*
769. *Mycoplasma verecundum*
770. *Mycoplasma vulturii*
771. *Mycoplasma wenyonii*
772. *Mycoplasma yeatsii*
773. *Mycoplasma zalophi*
774. *Toxoplasma gondii*
775. *Chlamydia suis*
776. *Chlamydia trachomatis*
777. Fungal infections A further group of diseases for the treatment and/or prevention of which the CD3 kappa peptides and the nucleic acids coding therefor, respectively, and in particular the CD3 kappa peptide related compounds are used in a preferred embodiment, are those where the surface expression of the TCR is abundant, more particularly higher than expected under normal or non-diseased conditions, or where the surface expression of the TCR is found in lymphocytes in compartments where in the healthy subjects a lower TCR expression can be found. CD3 kappa peptides and the nucleic acids coding therefor, respectively, and in particular the CD3 kappa peptide related compounds are used in the treatment of higher expression of named antiapoptotic and/or proliferation inducing receptors, and/or the named cytokines.

In other words, the CD3 kappa peptides and the nucleic acids coding therefor, respectively, and in particular the CD3 kappa peptide related compounds are used in an embodiment for the treatment and/or prevention of a disease where the increased or prolonged surface expression of the T cell receptor, and/or the antiapoptotic, and/or proliferation inducing receptors recited herein, and/or the cytokines recited herein, gives rise to, is linked to or is associates with a pathological condition which is the respective disease, a pre-stage thereof or which increases the susceptibility of a subject for such disease. Such diseases are preferably autoimmune diseases and more preferably selected from the group comprising the diseases summarized in table 2.

TABLE 2

| Autoimmune disorders which can be treated in accordance with the present Invention | |
|---|---|
| 1. | Takayasu Arteritis |
| 2. | Giant-cell arteritis |
| 3. | familial mediterranean fever |
| 4. | Kawasaki disease |
| 5. | Polyarteritis nodosa |
| 6. | cutanous Polyarteritis nodosa |
| 7. | Hepatitis-associated arteritis |
| 8. | Behcet's syndrome |
| 9. | Wegener's granulomatosis |
| 10. | Churg-Strauss syndrome |
| 11. | microscopic polyangiitis |
| 12. | Vasculitis of connective tissue diseases |
| 13. | Hennoch-Schonlein purpura |
| 14. | Cryoglobulinemic vasculitis |
| 15. | Cutaneous leukocytoclastic angiitis |
| 16. | Tropical aortitis |
| 17. | Sarcoidosis |
| 18. | Cogan's syndrome |
| 19. | Wiskott-Aldrich Syndrome |
| 20. | Lepromatous arteritis |
| 21. | Primary angiitis of the CNS |
| 22. | Thromboangiitis obliterans |
| 23. | Paraneoplastic ateritis |
| 24. | Urticaria |
| 25. | Dego's disease |
| 26. | Myelodysplastic syndrome |

TABLE 2-continued

| Autoimmune disorders which can be treated in accordance with the present Invention | |
|---|---|
| 27. | Eythema elevatum diutinum |
| 28. | Hyperimmunoglobulin D |
| 29. | Allergic Rhinitis |
| 30. | Asthma bronchiale |
| 31. | chronic obstructive pulmonary disease |
| 32. | periodontitis |
| 33. | Rheumatoid Arthritis |
| 34. | atherosclerosis |
| 35. | Amyloidosis |
| 36. | Morbus Chron |
| 37. | Colitis ulcerosa |
| 38. | Autoimmune Myositis |
| 39. | Diabetes mellitus |
| 40. | Multiple sclerosis |
| 41. | Guillain-Barre Syndrome |
| 42. | histiocytosis |
| 43. | Osteoarthritis |
| 44. | atopic dermatitis |
| 45. | periodontitis |
| 46. | chronic rhinosinusitis |
| 47. | Psoriasis |
| 48. | psoriatic arthritis |
| 49. | Microscopic colitis |
| 50. | Pulmonary fibrosis |
| 51. | glomerulonephritis |
| 52. | Whipple's disease |
| 53. | Still's disease |
| 54. | erythema nodosum |
| 55. | otitis |
| 56. | cryoglobulinemia |
| 57. | Sjogren's syndrome |
| 58. | Lupus erythematosus |
| 59. | aplastic anemia |
| 60. | Osteomyelofibrosis |
| 61. | chronic inflammatory demyelinating polyneuropathy |
| 62. | Kimura's disease |
| 63. | systemic sclerosis |
| 64. | chronic periaortitis |
| 65. | chronic prostatitis |
| 66. | idiopathic pulmonary fibrosis |
| 67. | chronic granulomatous disease |
| 68. | Idiopathic achalasia |
| 69. | bleomycin-induced lung inflammation |
| 70. | cytarabine-induced lung inflammation |
| 71. | Autoimmunthrombozytopenia |
| 72. | Autoimmunneutropenia |
| 73. | Autoimmunhemolytic anemia |
| 74. | Autoimmunlymphocytopenia |
| 75. | Chagas' disease |
| 76. | chronic autoimmune thyroiditis |
| 77. | autoimmune hepatitis |
| 78. | Hashimoto's thyroiditis |
| 79. | atropic thyroiditis |
| 80. | Graves disase |
| 81. | Autoimmune polyglandular syndrome |
| 82. | Autoimmune Addison Syndrome |
| 83. | Pemphigus vulgaris |
| 84. | Pemphigus foliaceus |
| 85. | Dermatitis herpetiformis |
| 86. | Autoimmune alopecia |
| 87. | Vitiligo |

TABLE 2-continued

| Autoimmune disorders which can be treated in accordance with the present Invention | |
|---|---|
| 88. | Antiphospholipid syndrome |
| 89. | Myasthenia gravis |
| 90. | Stiff-man syndrome |
| 91. | Goodpasture's syndrome |
| 92. | Sympathetic ophthalmia |
| 93. | Folliculitis |
| 94. | Sharp syndrome |
| 95. | Evans syndrome |

It will be acknowledged by the one skilled in the art that particularly those diseases where the T cell receptor surface expression is to be reduced for achieving a therapeutically beneficial effect, CD3 kappa peptide related compounds can be advantageously used, whereby such CD3 kappa peptide related compounds are targeting or interacting wild type CD3 kappa peptide, preferably the CD3 kappa peptide according to SEQ ID NO:4, and any nucleic acids coding therefor. Such compounds are preferably selected from the group comprising small molecules, antibodies, high affinity binding peptides, anticalines, aptamers, spiegelmers, antisense-nucleic acids, ribozymes and RNAi molecules which are described herein in more detail.

The use of the CD3 kappa peptide and the nucleic acids coding therefor, for this kind of disease is, in principle, also possible under the proviso that the administration of an analogue of CD3 kappa or a nucleic acid coding therefor results in the blocking of the physiologically present CD3 kappa peptide. Preferably such analogue has an amino acid sequence according to SEQ ID NOs. 5-4437. A possible explanation for this effect is competitive inhibition. In connection therewith particularly those derivatives of CD3 kappa peptides are advantageous and can be advantageously used which do not have one, preferably more and most preferably all of the characteristics of the CD3 kappa peptide having the amino acid sequence according to SEQ ID NO:4.

Additionally, the diseases which can be addressed, i.e. treated or prevented, by either using the CD3 kappa peptides and nucleic acids coding therefor such as by, e.g., the aforementioned mechanism of competitive inhibition, or by the CD3 kappa peptide related compounds, may also be defined by the further effects of CD3 kappa, in particular the effect of the CD3 kappa peptide having amino acid sequence according to SEQ ID NO:4. This is based on the further surprising finding of the present inventors that an increased titre of CD3 kappa having the amino acid sequence according to SEQ ID NO:4 goes along with or is associated with an increased expression of CD4, CD2, CD25, CD116, CD127, CCR5, CCR9, CXCR1, CXCR3, EGF, Eotaxin-2, I-309, IFN-gamma, IL-1alpha, IL-1 beta, IL-3, IL-6, NAP-2, TGF-beta3, and PARC. Preferably, the increase in the expression of CD4, CD2, CD25, CD116, CD127, CCR5, CCR9, CXCR1, CXCR3 after CD3 kappa peptide treatment, preferably within 48 hours, by at least a factor of 50%, more preferably by at least 100% and even more preferably by at least 200%. The increase in the expression of the proinflammatory cytokines and chemokines EGF, Eotaxin-2, I-309, IL-1β, IL-3, IL-6, NAP-2, TGFβ3 and PARC after CD3 kappa peptide treatment, preferably within 48 hours, is by at least a factor of 50%, more preferably at least 100% and even more preferably at least 200%. The increase in the expression of IL-1α and IFNγ after CD3 kappa peptide treatment, preferably within 48 hours, is by at least a factor of 100%, more preferably at least 200% and even more preferably at least 500%.

More specifically, any disease which goes along with the decreased expression of these proteins can thus be prevented and/or treated using the CD3 kappa peptide and the respective nucleic acid coding therefor. The particular diseases to be thus treated or prevented can be more specifically taken from the mode of action of any of these cytokines and chemokines. Accordingly, as outlined above, all infections caused by or associated with viruses or intracellular pathogens as those listed in table 1 can be treated with CD3 kappa peptides or nucleic acids coding therefor. The following table 3 summarized some of the diseases which can accordingly be treated and prevented, respectively.

TABLE 3

| Further diseases which can be treated using CD3 kappa peptides and nucleic acids coding therefor (in addition to table 1). | |
|---|---|
| 1. | Chronic granulomatous disease |
| 2. | Chediak-Higashi syndrome |
| 3. | Leukocyte adhesion defect |
| 4. | Complement deficiencies |
| 5. | NK cell defect |
| 6. | X-linked hyper-IgM syndrome |
| 7. | Common variable immunodeficiency |
| 8. | Selective IgA deficiency |
| 9. | X-linked agammaglobulinemia (XLA) |
| 10. | Wiskott-Aldrich Syndrome |
| 11. | Bare lymphocyte syndrome (Class I) |
| 12. | Bare lymphocyte syndrome (Class II) |
| 13. | DiGeorge's syndrome |
| 14. | Severe Combined Immune Deficiency (SCID) |
| 15. | X-linked lymphoproliferative syndrome |
| 16. | Ataxia telangiectasia |
| 17. | Bloom's syndrome |
| 18. | Zap-70 deficiency |
| 19. | Purine nucleoside phosphorylase (PNP) deficiency |
| 20. | Nezelof syndrome |
| 21. | CD3ε and CD3γ deficiencies |
| 22. | Omenn syndrome |
| 23. | Reticular dysgenesis |
| 24. | Adenosine deaminase (ADA) deficiency |
| 25. | JAK3 deficiency |
| 26. | TAP2 deficiency |
| 27. | CIITA, RFX, and RFXAP deficiencies |
| 28. | Fanconi anaemia |
| 29. | Xeroderma pigmentosum |
| 30. | Nijmegen breakage syndrome |

It will also be acknowledged by the ones skilled in the art that some of the diseases mediated through or associated with these cytokines, chemokines or the said receptors, may be identical to or overlapping to the specific diseases disclosed herein. However, in any case such diseases will be obvious to the one skilled in the art in the light of the present disclosure.

In a similar way as the inventors defined above the characteristics of what is preferably understood herein by the term "decreased expression of the TCR" and the capability of the CD3 kappa peptides and nucleic acids coding therefor to normalize and/or increase the expression thereof, particularly in connection with the various diseases related thereto and as disclosed herein, this can also be done to show the beneficial effect in regards to the expression of the proinflammatory cytokines and chemokines, and of the said receptors going along with such decreased expression of the TCR as disclosed herein.

Insofar, the difference in expression between patients and healthy subjects should preferably be the mean value of the expression of the said proinflammatory cytokines and chemokines, and of the said receptors of the healthy subjects plus three times the standard deviation, or should also possibly be congruent to statistical hypothesis testing with a p-value of or below 0.05, making the difference statistically significant.

Also using this criterion, the present inventors have found that the expression of the said proinflammatory cytokines and chemokines, and of the respective said receptors in the leukocytes in the patient populations described herein can be increased by CD3 kappa peptides, its derivatives and nucleic acids coding therefor to normal values as defined by healthy individuals.

Additionally, the diseases which can be addressed, i.e. treated or prevented, by either using the CD3 kappa peptides and nucleic acids coding therefor, may also be defined by the further effects of CD3 kappa disclosed herein, in particular the effect of the CD3 kappa peptide having amino acid sequence according to SEQ ID NO:4 residing in the decrease of the expression of a compound selected from the group comprising CD58, IL-1ra, IL-8, RANTES, SDF-1, TARC, MCP-4, GRO, soluble IL-6 receptor and soluble TNF-receptor II. This is based on the further surprising finding of the present inventors that an increased titre of CD3 kappa having the amino acid sequence according to SEQ ID NO:4 goes along with or is associated with a decreased expression of CD58, IL-1ra, IL-8, RANTES, SDF-1, TARC, MCP-4, GRO, soluble IL-6 receptor and soluble TNF-receptor II. More specifically, any disease which goes along with an increased expression of CD58, IL-1ra, IL-8, RANTES, SDF-1, TARC, MCP-4, GRO, soluble IL-6 receptor and soluble TNF-receptor II, respectively can thus be prevented and/or treated using the CD3 kappa peptides and the respective nucleic acid coding therefor. The decrease in the expression of those factors after CD3 kappa peptide treatment, preferably within 48 hours, is by at least a factor of 50%, more preferably at least 100% and even more preferably at least 200%. The particular diseases to be thus treated or prevented can be more specifically taken from the mode of action of any of these cytokines and chemokines and is, for example disclosed in Table 2 summarized some of the diseases which can accordingly be treated and prevented, respectively.

It will also be acknowledged by the ones skilled in the art that some of the diseases mediated through or associated with these cytokines and chemokines, respectively, may be identical to or overlapping to the specific diseases disclosed herein, however, in any case such diseases will be obvious to the one skilled in the art in the light of the present disclosure.

In the same way as the inventors defined above the characteristics of what is preferably understood herein by the term "decreased expression of the TCR" and the capability of the CD3 kappa peptides and nucleic acids coding therefor to normalize and/or increase the expression thereof, particularly in connection with the various diseases related thereto and as disclosed herein, this can also be done to show the beneficial effect in regards to the expression of the said cytokines and chemokines, and of CD58.

Insofar, the difference in expression between patients and healthy subjects should preferably be the mean value of the expression of the said cytokines and chemokines, and of CD58 of the healthy subjects plus three times the standard deviation, or should also possibly be congruent to statistical hypothesis testing with a p-value of or below 0.05, making the difference statistically significant.

Also having used this criterion, the present inventors have found that the expression of the said cytokines and chemokines, and of CD58 in the leukocytes in the patient populations described herein can be decreased by CD3 kappa peptides, its derivatives and nucleic acids coding therefor.

As disclosed herein the CD3 kappa peptides and the nucleic acids coding therefor, will be suitable to increase the TCR surface expression status of a patient and of a healthy subject. Insofar, any medicament comprising at least one of the CD3 kappa peptides and/or at least one of the nucleic acids coding therefor, can be used for restoring the immune status of a patient or subject, preferably healthy subject, also referred to herein together as person. Such person may be a person who has been, is or will be undergoing a treatment which results or may result in depletion of T cells and more specifically surface expression of the T cell receptor. This kind of person may thus be a person which has, is or will be undergoing chemotherapy, therapy with biologicals as antibodies, cytokines or other recombinant proteins, and radiation therapy, respectively. Another group of persons to which the CD3 kappa peptides and the nucleic acids coding therefor or any medicament or pharmaceutical composition comprising the same may or will be administered, is thus any person suffering from or being at the risk of suffering from a reduction or depletion of T cell receptor expression, whereby such reduced T cell receptor expression preferably results from a disease or a genetic disorder. Such genetic disorders are for example included in Table 3.

Again without wishing to be bound by any theory, the present inventors assume that CD3 kappa having the amino acid sequence according to SEQ ID NO:4 is suitable to direct T cells to secrete cytokines congruent to a $TH_0$ or $TH_1$ profile rather than to a $TH_2$ profile. Insofar, the use of the CD3 kappa peptides and the nucleic acids coding therefor, is also suitable in the prevention and/or treatment of any disease which is characterized by or can be prevented and/or treated by increasing the $TH_1$ response of a person, preferably a patient. Insofar, the CD3 kappa peptides and the nucleic acids coding therefor, can be used in vaccination. It is thus also within the present invention that the CD3 kappa peptides and the nucleic acids coding therefor, are used either alone or in combination as adjuvants.

It is within the present invention that any of the medicament and pharmaceutical composition, respectively, described herein comprising at least one of the pharmaceutically active compound according to the present invention herein may be used for the treatment and/or prevention of a diseases, preferably any of the diseases disclosed herein.

As preferably used herein, the term pharmaceutically active compound according to the present invention comprises one of the compounds selected from the group comprising CD3 kappa peptides, nucleic acids coding therefor and CD3 kappa peptide related compounds, whereby such CD3 kappa peptide related compounds also comprise small molecules. Preferably, as used herein, small molecules are molecules which are pharmaceutically active and fulfil the Lepinsky rules of five and, additionally and/or alternatively have a molecular weight of 1000 or less.

Apart from being used as ingredient of a pharmaceutical composition or for the manufacture of a medicament, particularly the CD3 kappa peptide related compounds are used in a preferred embodiment as diagnostics or means for diagnostic. This use of the CD3 kappa related compounds is based on the finding that CD3 kappa is overexpressed in connection with those diseases specified above. Insofar, these CD3 kappa related compounds are preferably useful in the diagnostic of diseases going along with an increased CD3 kappa peptide titre, preferably an increased titre of CD3 kappa having an amino acid sequence according to SEQ ID NO:4, or an increased transcription and/or translation of a nucleic acid sequence coding for CD3 kappa having the amino acid sequence according to SEQ ID NO:4.

When used as diagnostics the CD3 kappa peptide related compounds are either labelled so as to allow the detection thereof, or are further reacted with another compound detecting the CD3 kappa peptide related compound, preferably the CD3 kappa peptide related compound is complexed with either CD3 kappa, preferably CD3 kappa having the amino acid sequence according to SEQ ID NO:4, or a nucleic acid coding therefor. Preferably said another compound comprises a label or is adapted to allow the detection thereof.

It is within the present invention that in a preferred embodiment the terms disease and disorder are used in an interchangeable manner, if not indicated to the contrary.

It is also within the present invention that the pharmaceutically active compounds according to the present invention may be used for the treatment of a person or a patient suffering from a disease or diseased condition as defined above. Such treatment comprises the administration of one or several of the compounds according to the present invention or a medicament or pharmaceutical composition described herein. Preferably, the person is a mammal and most preferably a human being. In a further embodiment the person is in need of such treatment.

Depending on the specific conditions, disease or disorder to be treated, such pharmaceutically active compounds may be formulated and administrated systemically or locally. Techniques for formulation and administration may be found in "Remington's Pharmaceutical Sciences", 1990, $18^{th}$ ed., Mack Publishing Co., Easton, Pa. The administration of such pharmaceutically active compound according to the present invention can be done in a variety of ways, including, but not limited to, orally, subcutaneously, intravenously, intranasally, transdermally, intraperitoneally, intramuscularly, intrapulmonary, vaginally, rectally, or intraocularly, periocularly, intraorbitally, intracapsulary, intrasynovially, intracisternally, topically, just to name a few. In some instances, for example, in the treatment of wounds and inflammation, the compound according to the present invention may be directly applied as a ointment, powder, solution or spray. Topical administration also comprises passive or facilitated adsorption, preferably through the skin, including skin patches and ionophoresis.

In an embodiment of the various aspects of the present invention, a pharmaceutically active compound according to the present invention is administered together with a further pharmaceutically active compound.

Apart from being a potential drug itself, the CD3 kappa peptides and the nucleic acids coding therefor may be used as the compound against which chemical compounds may be used as drugs or drug candidates or as diagnostic agents, are directed. These chemical compounds belong to different classes of compounds such as antibodies, peptides, anticalines, aptamers, spiegelmers, ribozymes, antisense oligonucleotides and siRNA as well as small molecules which are also referred to herein in their entity as CD3 kappa peptide related compounds. The compounds are designed, selected, screened generated and/or manufactured by either using the CD3 kappa peptides and the nucleic acids coding therefor themselves as a physical or chemical entity, or information related to the CD3 kappa peptides and the nucleic acids coding therefor. Albeit it is referred to herein in the following mostly to the CD3 kappa peptides and the nucleic acids coding therefor in their entirety, it will be understood by the ones skilled in the art that preferably the CD3 kappa peptide having or comprising the amino acid sequence according to SEQ ID NO:4 and the nucleic acid(s) coding therefor will be the target(s) and, respectively, that the various classes of compounds will be addressing and interacting, respectively, with the CD3 kappa peptide having or comprising the amino acid sequence according to SEQ ID NO:4 and the nucleic acid(s) coding therefor. In the design, selection, screening, generation and/or manufacturing process of said classes of compounds the CD3 kappa peptides and the nucleic acids coding therefor will also be referred to as the target which is used in the process rather than in the final application of the respective compound to a patient in need thereof. In the processes which provide the various classes of compounds, either the CD3 kappa peptides or the nucleic acids coding therefor may be used. The term CD3 peptides as used herein comprises any fragment or derivative of the CD3 kappa peptide as disclosed herein which allows the design, selection, screening, generation and/or manufacture of said classes of compounds of the respective class(es) of compounds which in turn are/is upon their/its application as a medicament or as a diagnostic agent active as such. The term nucleic acid coding for the CD3 kappa peptides as used herein in connection with the CD3 kappa peptide related compounds shall comprise any nucleic acid which contains a nucleic acid which codes for the CD3 kappa peptides as defined above and herein, or a part thereof. A part of a nucleic acid coding for the CD3 kappa peptides is regarded as such as long as it is still suitable for the design, selection, screening, generation and/or manufacture of said classes of compounds which in turn are/is upon their/its application as a medicament or as a diagnostic agent active as such. The nucleic acid coding for the CD3 kappa peptides can be genomic nucleic acid, hnRNA, mRNA, cDNA or part of each thereof.

As outlined above it is within the present invention that apart from the CD3 kappa peptides or a part or derivative thereof or a nucleic acid sequence coding therefor, as described herein, also other means or compounds may be used in order to create or to suppress the effects arising from the CD3 kappa peptide having the amino acid sequence according to SEQ ID NO:4 or the nucleic acid coding therefor. Such means may be determined or selected in a screening method. In such screening method a first step is to provide one or several so called candidate compounds. Candidate compounds as used herein are compounds the suitability of which is to be tested in a test system for treating or alleviating the various diseases as described herein and diseased conditions as described herein or to be used as a diagnostic means or agent for this kind of diseases and diseased conditions. If a candidate compound shows a respective effect in a test system said candidate compound is a suitable means or agent for the treatment of said diseases and diseased conditions and, in principle, as well a suitable diagnostic agent for said diseases and diseased conditions. In a second step the candidate compound is contacted with a CD3 kappa peptides expression system or a CD3 kappa peptides gene product, preferably a respective gene expression product, such as a hnRNA or mRNA coding for CD3 kappa having an amino acid sequence according the SEQ ID NO:4, or a CD3 kappa peptides activity system or one of the CD3 kappa peptides, preferably the CD3 kappa having an amino acid sequence according to SEQ ID NO:4. The CD3 kappa peptides activity system is also referred to herein as and/or is preferably also active in the meaning of a system detecting the activity of a CD3 kappa peptides, more preferably of CD3 kappa having an amino acid sequence according to SEQ ID NO:4.

An expression system for CD3 kappa peptides is basically an expression system which shows or displays the expression of one of the CD3 kappa peptides, preferably of CD3 kappa having an amino acid sequence according to SEQ ID NO:4, whereby the extent or level of expression basically may be changed. Preferably, a CD3 kappa peptides activity system is essentially an expression system, whereby the activity or condition of activity is measured rather than the expression of a CD3 kappa peptide. Alternatively, a CD3 kappa peptide activity system is a CD3 kappa peptide system whereby the activity of such CD3 kappa peptide can be measured, or a system providing or comprising a CD3 kappa peptide. In any of these systems it is tested whether under the influence of a candidate compound the activity of a CD3 kappa peptide and more preferably of CD3 kappa having the amino acid sequence according to SEQ ID NO:4 or of the nucleic acid coding therefor, is different from the situation without the candidate compound. Regardless whether the particular system is either an expression system or an activity system, it is within the scope of the present invention that either an increase or a decrease of the activity and expression, respectively, may occur and be measured. Preferably, the expression system and/or activity system is an in vitro reaction using sub-cellular means, such as a cell extract or a fraction of the cell extract such as a nucleus extract. A CD3 kappa peptide expression system as used herein may also be a cell, preferably a cell of a tissue or organ involved in the diseases as described herein and diseased conditions as described herein.

Whether there is an increase or decrease in the activity system or expression system, may be determined at each level of the expression, for example by measuring the increase or decrease of the amount of nucleic acid coding for a CD3 kappa peptides, preferably CD3 kappa having an amino acid sequence according to SEQ ID NO:4, more particularly mRNA or the increase or decrease of a CD3 kappa peptide, preferably CD3 kappa having an amino acid sequence according to SEQ ID NO:4 expressed under the influence of the candidate compound. The techniques required for the measurement, more particularly the quantitative measurement of this kind of changes, such as for the mRNA or the protein are known to the one skilled in the art. Also known to the one skilled in the art are methods to determine the amount of or content of CD3 kappa peptides, preferably CD3 kappa having an amino acid sequence according to SEQ ID NO:4, e.g. by the use of appropriate antibodies. Antibodies may be generated as known to the one skilled in the art and described, e.g. by Harlow, E., and Lane, D., "Antibodies: A Laboratory Manual," Cold Spring Harbor Laboratory, Cold Spring Harbor, N.Y., (1988).

In case of a CD3 kappa peptide expression system, whereby preferably the CD3 kappa peptide is CD3 kappa having an amino acid sequence according to SEQ ID NO:5, an increase or decrease of the activity of a CD3 kappa peptide, preferably CD3 kappa having an amino acid sequence according to SEQ ID NO:4 may be determined, preferably in a functional assay.

Contacting the candidate compound and the expression system and activity system, respectively, is usually performed by adding an aqueous solution of the candidate compound to a respective reaction system which is generally referred to herein as test system. Besides aqueous solutions also suspensions or solutions of the candidate compound in organic solvents may be used. The aqueous solution is preferably a buffer solution.

Preferably, in each run using the expression system and activity system, respectively, only a single candidate compound is used. However, it is also within the present invention that several of these tests are performed in parallel in a high throughput system.

A further step in the method according to the present invention resides in determining whether under the influence of the candidate compound the expression or activity of the expression system and activity system, respectively, in relation to a CD3 kappa peptide, preferably CD3 kappa having an amino acid sequence according to SEQ ID NO:4 or a nucleic acid coding therefore, is changed. Typically this is done by comparing the system's reaction upon addition of the candidate compound relative to the one without addition of the candidate compound. Preferably, the candidate compound is a member of a library of compounds.

Basically any library of compounds is suitable for the purpose of this invention regardless of the class of compounds. Suitable libraries of compounds are, among others, libraries composed of small molecules, of peptides, proteins, antibodies, anticalines and functional nucleic acids. The latter compounds may be generated as known to the one skilled in the art and outlined herein.

The manufacture of an antibody specific for the a CD3 kappa peptides having an amino acid or for the nucleic acids coding therefore, is known to the one skilled in the art and, for example, described in Harlow, E., and Lane, D., "Antibodies: A Laboratory Manual," Cold Spring Harbor Laboratory, Cold Spring Harbor, N.Y., (1988). Preferably, monoclonal antibodies may be used in connection with the present invention which may be manufactured according to the protocol of Köhler and Milstein and further developments based thereon. Antibodies as used herein include, but are not limited to, complete antibodies, antibody fragments or derivatives such as Fab fragments, Fc fragments and single-stranded antibodies, as long as they are suitable and capable of binding to the CD3 kappa peptides. Apart from monoclonal antibodies also polyclonal antibodies may be used and/or generated. The generation of polyclonal antibodies is also known to the one skilled in the art and, for example, described in Harlow, E., and Lane, D., "Antibodies: A Laboratory Manual," Cold Spring Harbor Laboratory, Cold Spring Harbor, N.Y., (1988). Preferably, the antibodies used for therapeutical purposes are humanized or human antibodies as defined above.

The antibodies which may be used according to the present invention may have one or several markers or labels. Such markers or labels may be useful for detecting the antibody either in its diagnostic application or its therapeutic application. Preferably the markers and labels are selected from the group comprising avidine, streptavidine, biotin, gold and fluorescein and used, e.g., in ELISA methods. These and further markers as well as methods are, e.g., described in Harlow, E., and Lane, D., "Antibodies: A Laboratory Manual," Cold Spring Harbor Laboratory, Cold Spring Harbor, N.Y., (1988).

It is also within the present invention that the label or marker exhibits an additional function apart from detection, such as interaction with other molecules. Such interaction may be, e.g., specific interaction with other compounds. These other compounds may either be those inherent to the system where the antibody is used such as the human or animal body or the sample which is analyzed by using the respective antibody. Appropriate markers may, for example, be biotin or fluoresceine with the specific interaction partners thereof such as avidine and streptavidine and the like being present on the respective compound or structure to interact with the thus marked or labelled antibody.

Further classes of medicaments as well as diagnostic agents which may be generated using the CD3 kappa peptides or the nucleic acid coding therefor, are peptides which bind thereto. Such peptides may be generated by using methods according to the state of the art such as phage display. Basically, a library of peptide is generated, such as in form of phages, and this kind of libraries is contacted with the target molecule, in the present case, for example, the CD3 kappa peptides. Those peptides binding to the target molecule, i.e. one of the CD3 kappa peptides, are subsequently removed, preferably as a complex with the target molecule, from the respective reaction. It is known to the one skilled in the art that the binding characteristics, at least to a certain extend, depend on the particularly realized experimental set-up such as the salt concentration and the like. After separating those peptides binding to the target molecule with a higher affinity or a bigger force, from the non-binding members of the library, and optionally also after removal of the target molecule from the complex of target molecule and peptide, the respective peptide(s) may subsequently be characterised. Prior to the characterisation optionally an amplification step is realized such as, e.g. by propagating the peptide coding phages. The characterisation preferably comprises the sequencing of the target binding peptides. Basically, the peptides are not limited in their lengths, however, preferably peptides having a lengths from about 8 to 20 amino acids are preferably obtained in the respective methods. The size of the libraries may be about $10^2$ to $10^{18}$, preferably $10^8$ to $10^{15}$ different peptides, however, is not limited thereto. The thus identified peptides are also preferably referred to as peptide aptamers.

A particular form of target binding polypeptides are the so-called “anticalines” which are, among others, described in German patent application DE 197 42 706.

According to the present invention the protein of the CD3 kappa peptides and the nucleic acid(s) coding therefor may be used as the target for the manufacture or development of a medicament for the treatment of the diseases described herein and of the diseased conditions described herein, as well as for the manufacture and/or development of means for the diagnosis of said diseases and said conditions, in a screening process, whereby in the screening process small molecules or libraries of small molecules are used. This screening comprises the step of contacting the target molecule with a single small molecule or a variety of small molecules at the same time or subsequently, preferably those from the library as specified above, and identifying those small molecules or members of the library which bind to the target molecules which, if screened in connection with other small molecules may be separated from the non-binding or non-interacting small molecules. It will be acknowledged that the binding and non-binding may strongly be influenced by the particular experimental set-up. In modifying the stringency of the reaction parameters it is possible to vary the degree of binding and non-binding which allows a fine tuning of this screening process. Preferably, after the identification of one or several small molecules which specifically interact with the target molecule, this small molecule may be further characterised. This further characterisation may, for example, reside in the identification of the small molecule and determination of its molecule structure and further physical, chemical, biological and/or medical characteristics. Preferably, the natural compounds have a molecular weight of about 100 to 1000 Da. Also preferably, small molecules are those which comply with the Lepinsky rules of five known to the ones skilled in the art. Alternatively, small molecules may also be defined such that they are synthetic-small-molecules, preferably arising from combinatorial chemistry, in contrast to natural products which preferably are non-synthetic. However, it is to be noted that these definitions are only subsidiary to the general understanding of the respective terms in the art.

It is also within the present invention to use the CD3 kappa peptides and the nucleic acid(s) coding therefor as a target molecule for the manufacture or selection of aptamers and spiegelmers which may then be used directly or indirectly either as medicament or as diagnostic agents.

Aptamers are D-nucleic acids which are either single stranded or double stranded which specifically interact with a target molecule. The manufacture or selection of aptamers is, e.g., described in European patent EP 0 533 838. Basically the following steps are realized. First, a mixture of nucleic acids, i.e. potential aptamers, is provided whereby each nucleic acid typically comprises a segment of several, preferably at least eight subsequent randomised nucleotides. This mixture is subsequently contacted with the target molecule whereby the nucleic acid(s) bind to the target molecule, such as based on an increased affinity towards the target or with a bigger force thereto, compared to the candidate mixture. The binding nucleic acid(s) are/is subsequently separated from the remainder of the mixture. Optionally, the thus obtained nucleic acid(s) is amplified using, e.g. polymerase chain reaction. These steps may be repeated several times giving at the end a mixture having an increased ratio of nucleic acids specifically binding to the target from which the final binding nucleic acid is then optionally selected. These specifically binding nucleic acid(s) are referred to aptamers. It is obvious that at any stage of the method for the generation or identification of the aptamers samples of the mixture of individual nucleic acids may be taken to determine the sequence thereof using standard techniques. It is within the present invention that the aptamers may be stabilized such as, e.g., by introducing defined chemical groups which are known to the one skilled in the art of generating aptamers. Such modification may for example reside in the introduction of an amino group at the 2'-position of the sugar moiety of the nucleotides. Aptamers are currently used as therapeutic agents. However, it is also within the present invention that the thus selected or generated aptamers may be used for target validation and/or as lead substance for the development of medicaments, preferably of medicaments based on small molecules. This is actually done by a competition assay whereby the specific interaction between the target molecule and the aptamer is inhibited by a candidate drug whereby upon replacement of the aptamer from the complex of target and aptamer it may be assumed that the respective drug candidate allows a specific inhibition of the interaction between target and aptamer, and if the interaction is specific, said candidate drug will, at least in principle, be suitable to block the target and thus decrease its biological availability or activity in a respective system comprising such target. The thus obtained small molecule may then be subject to further derivatization and modification to optimise its physical, chemical, biological and/or medical characteristics such as toxicity, specificity, biodegradability and bioavailability.

The generation or manufacture of spiegelmers which may be used or generated according to the present invention using the CD3 kappa peptides or a nucleic acid coding therefor, is based on a similar principle. The manufacture of spiegelmers is described in the international patent application WO 98/08856. Spiegelmers are L-nucleic acids, which means that they are composed of L-nucleotides rather than aptamers which are composed of D-nucleotides as aptamers are. Spiegelmers are characterized by the fact that they have a very high stability in biological system and, comparable to aptamers, specifically interact with the target molecule against which they are directed which is for the purpose of this invention and if not indicated to the contrary, (a/the) CD3 kappa peptide(s) and the nucleic acids coding therefor. In the purpose of generating spiegelmers, a heterogonous population of D-nucleic acids is created and this population is contacted with the optical antipode of the target molecule, in the present case for example with the D-enantiomer of the naturally occurring L-enantiomer of the CD3 kappa peptides. Subsequently, those D-nucleic acids are separated which do not interact with the optical antipode of the target molecule. However, those D-nucleic acids interacting with the optical antipode of the target molecule are separated, optionally determined and/or sequenced and subsequently the corresponding L-nucleic acids are synthesized based on the nucleic acid sequence information obtained from the D-nucleic acids. These L-nucleic acids which are identical in terms of sequence with the aforementioned D-nucleic acids interacting with the optical antipode of the target molecule will specifically interact with the naturally occurring target molecule rather than with the optical antipode thereof. Similar to the method for the generation of aptamers it is also possible to repeat the various steps several times and thus to enrich those nucleic acids specifically interacting with the optical antipode of the target molecule.

The inventors want specially emphasize that the development of spiegelmers which bind to the CD3 kappa peptides is technically feasible because CD3 kappa peptides can be synthesized from L-amino acid compounds, whereby a synthesis of CD3 kappa peptides consisting of or containing D-amino acids is procurable. These CD3 kappa peptides consisting of or containing D-amino acids can be purified to 99,999% purity and produced in high amounts. A screening to generate spiegelmers with L-nucleic acids is therefore rapidly performed. The development and application of CD3 kappa binding spiegelmers to treat autoimmune diseases as those listed in table 2 is therefore safer to perform and is safer for patients as the application of a monoclonal antibody.

A further class of compounds which may be manufactured or generating based on the CD3 kappa peptides and in particular on the nucleic acids coding therefor, as the target molecule as disclosed herein, are ribozymes, antisense oligonucleotides and siRNA.

It is a common feature of all of the aforementioned nucleic acids that they do not interact with the target molecule at the level of the translation product which are in the present case the CD3 kappa peptides, but rather interact with the transcription product, i.e. the nucleic acid coding therefor such as the genomic nucleic acid or any nucleic acid derived there from such as the corresponding hnRNA, cDNA and mRNA, respectively. Insofar, the target molecule of the aforementioned class of compounds is preferably the mRNA of CD3 kappa. Most specifically these compounds are directed against the fusion region of CD3 kappa corresponding to the region encoded by exon 1, the part of exon 2 and exon 4 to prevent effects on the expression of CD3 delta.

Ribozymes are catalytically active nucleic acids which preferably consist of RNA which basically comprises two moieties. The first moiety shows a catalytic activity whereas the second moiety is responsible for the specific interaction with the target nucleic acid, in the present case the nucleic acids coding for the CD3 kappa peptides. Upon interaction between the target nucleic acid and the second moiety of the ribozyme, typically by hybridisation and Watson-Crick base pairing of essentially complementary stretches of bases on the two hybridising strands, the catalytically active moiety may become active which means that it catalyses, either intramolecularly or intermolecularly, the target nucleic acid in case the catalytic activity of the ribozyme is a phosphodiesterase activity. Subsequently, there may be a further degradation of the target nucleic acid which in the end results in the degradation of the target nucleic acid as well as the protein derived from the said target nucleic acid which in the present case are the CD3 kappa peptides due to a lack of newly synthesized CD3 kappa peptides and a turn-over of prior existing the CD3 kappa peptides. Ribozymes, their use and design principles are known to the one skilled in the art, and, for example described in Doherty and Doudna (Ribozym structures and mechanism. Annu ref. Biophys. Biomolstruct. 2001; 30:457-75) and Lewin and Hauswirth (Ribozyme Gene Therapy: Applications for molecular medicine. 2001 7:221-8).

The use of antisense oligonucleotides for the manufacture of a medicament and as a diagnostic agent, respectively, is based on a similar mode of action. Basically, antisense oligonucleotides hybridise based on base complementarity, with a target RNA, preferably with a mRNA, thereby activate RNase H. RNase H is activated by both phosphodiester and phosphorothioate-coupled DNA. Phosphodiester-coupled DNA, however, is rapidly degraded by cellular nucleases with the exception of phosphorothioate-coupled DNA. These resistant, non-naturally occurring DNA derivatives do not inhibit RNase H upon hybridisation with RNA. In other words, antisense polynucleotides are only effective as DNA:RNA hybride complexes. Examples for this kind of antisense oligonucleotides are described, among others, in U.S.-patent U.S. Pat. No. 5,849,902 and U.S. Pat. No. 5,989,912. In other words, based on the nucleic acid sequence of the target molecule which in the present case are the nucleic acids coding for the CD3 kappa peptides, either from the target protein from which a respective nucleic acid sequence may in principle be deduced, or by knowing the nucleic acid sequence as such, particularly the mRNA, suitable antisense oligonucleotides may be designed base on the principle of base complementarity.

Particularly preferred are antisense-oligonucleotides which have a short stretch of phosphorothioate DNA (3 to 9 bases). A minimum of 3 DNA bases is required for activation of bacterial RNase H and a minimum of 5 bases is required for mammalian RNase H activation. In these chimeric oligonucleotides there is a central region that forms a substrate for RNase H that is flanked by hybridising "arms" comprised of modified nucleotides that do not form substrates for RNase H. The hybridising arms of the chimeric oligonucleotides may be modified such as by 2'-O-methyl or 2'-fluoro. Alternative approaches use methylphosphonate or phosphoramidate linkages in said arms. Further embodiments of the antisense oligonucleotide useful in the practice of the present invention are P-methoxyoligonucleotides, partial P-methoxyoligodeoxyribonucleotides or P-methoxyoligonucleotides.

Of particular relevance and usefulness for the present invention are those antisense oligonucleotides as more particularly described in the above two mentioned U.S. patents. These oligonucleotides contain no naturally occurring 5'→3'-linked nucleotides. Rather the oligonucleotides have two types of nucleotides: 2'-deoxyphosphorothioate, which activate RNase H, and 2'-modified nucleotides, which do not. The linkages between the 2'-modified nucleotides can be phosphodiesters, phosphorothioate or P-ethoxyphosphodiester. Activation of RNase H is accomplished by a contiguous RNase H-activating region, which contains between 3 and 5 2'-deoxyphosphorothioate nucleotides to activate bacterial RNase H and between 5 and 10 2'-deoxyphosphorothioate nucleotides to activate eukaryotic and, particularly, mammalian RNase H. Protection from degradation is accomplished by making the 5' and 3' terminal bases highly nuclease resistant and, optionally, by placing a 3' terminal blocking group.

More particularly, the antisense oligonucleotide comprises a 5' terminus and a 3' terminus; and from 11 to 59 5'→3'-linked nucleotides independently selected from the group consisting of 2'-modified phosphodiester nucleotides and 2'-modified P-alkyloxyphosphotriester nucleotides; and wherein the 5'-terminal nucleoside is attached to an RNase H-activating region of between three and ten contiguous phosphorothioate-linked deoxyribonucleotides, and wherein the 3'-terminus of said oligonucleotide is selected from the group consisting of an inverted deoxyribonucleotide, a contiguous stretch of one to three phosphorothioate 2'-modified ribonucleotides, a biotin group and a P-alkyloxyphosphotriester nucleotide.

Also an antisense oligonucleotide may be used wherein not the 5' terminal nucleoside is attached to an RNase H-activating region but the 3' terminal nucleoside as specified above. Also, the 5' terminus is selected from the particular group rather than the 3' terminus of said oligonucleotide.

Suitable and useful antisense oligonucleotides are also those comprising a 5' terminal RNase H activating region and having between 5 and 10 contiguous deoxyphosphorothioate nucleotides; between 11 to 59 contiguous 5'→3'-linked 2'-methoxyribonucleotides; and an exonuclease blocking group present at the 3' end of the oligonucleotide that is drawn from the group consisting of a non-5'-3'-phosphodiester-linked nucleotide, from one to three contiguous 5'-3'-linked modified nucleotides and a non-nucleotide chemical blocking group.

Two classes of particularly preferred antisense oligonucleotides can be characterized as follows:

The first class of antisense oligonucleotides, also referred to herein as second generation of antisense oligonucleotides, comprises a total of 23 nucleotides comprising in 5'→3' direction a stretch of seven 2'-O-methylribonucleotides, a stretch of nine 2'-deoxyribonucleotides, a stretch of six 2'-O-methylribonucleotides and a 3'-terminal 2'-deoxyribonucleotide. From the first group of seven 2'-O-methylribonucleotides the first four are phosphorothioate linked, whereas the subsequent four 2'-O-methylribonucleotides are phosphodiester linked. Also, there is a phosphodiester linkage between the last, i.e. the most 3'-terminal end of the 2'-O-methylribonucleotides and the first nucleotide of the stretch consisting of nine 2'-deoxyribonucleotides. All of the 2'-deoxyribonucleotides are phosphorothioate linked. A phosphorothioate linkage is also present between the last, i.e. the most 3'-terminal 2'-deoxynucleotide, and the first 2'-O-methylribonucleotide of the subsequent stretch consisting of six 2'-O-methylribonucleotides. From this group of six 2'-O-methylribonucleotides the first four of them, again in 5'→3' direction, are phosphodiester linked, whereas the last three of them, corresponding to positions 20 to 22 are phosphorothioate linked. The last, i.e. terminal 3'-terminal 2'-deoxynucleotide is linked to the last, i.e. most 3'-terminal 2'-O-methylribonucleotide through a phosphorothioate linkage.

This first class may also be described by reference to the following schematic structure: RRRnnnnNNNNNNNNNnnnRRRN. Hereby, R indicates phosphorothioate linked 2'-O-methyl ribonucleotides (A, G, U, C); n stands for 2'-O-methyl ribonucleotides (A, G, U, C); N represents phosphorothioate linked deoxyribonucleotides (A, G, T, C).

The second class of particularly preferred antisense oligonucleotides, also referred to herein as third generation (of) antisense oligonucleotides or GeneBlocs, also comprises a total of 17 to 23 nucleotides with the following basic structure (in 5'→3' direction).

At the 5'-terminal end there is an inverted abasic nucleotide which is a structure suitable to confer resistance against exonuclease activity and, e.g., described in WO 99/54459. This inverted abasic nucleotide is linked to a stretch of five to seven 2'-O-methylribonucleotides which are phosphodiester linked. Following this stretch of five to seven 2'-O-methylribonucleotides there is a stretch of seven to nine 2'-deoxyribonucleotides all of which are phosphorothioate linked. The linkage between the last, i.e. the most 3'-terminal 2'-O-methylribonucleotide and the first 2'-deoxynucleotide of the 2'-deoxynucleotide comprising stretch occurs via a phosphodiester linkage. Adjacent to the stretch of seven to nine 2'-deoxynucleotides a stretch consistent of five to seven 2'-O-methylribonucleotides is connected. The last 2'-deoxynucleotide is linked to the first 2'-O-methylribonucleotide of the latter mentioned stretch consisting of five to seven 2'-O-methylribonucleotides occurs via a phosphorothioate linkage. The stretch of five to seven 2'-O-methylribonucleotides are phosphodiester linked. At the 3'-terminal end of the second stretch of five to seven 2'-O-methylribonucleotide another inverted abasic nucleotide is attached.

This second class may also be described by reference to the following schematic structure: (GeneBlocs representing the 3rd generation of antisense oligonucleotides have also the following schematic structure:) cap-$(n_p)_x(N_s)_y(n_p)_z$-cap or cap-nnnnnnnNNNNNNNNNnnnnnnn-cap. Hereby, cap represents inverted deoxy abasics or similar modifications at both ends; n stands for 2'-O-methyl ribonucleotides (A, G, U, C); N represents phosphorothioate-linked deoxyribonucleoties (A, G, T, C); x represents an integer from 5 to 7; y represents an integer from 7 to 9; and z represents an integer from 5 to 7.

It is to be noted that the integers x, y and z may be chosen independently from each other although it is preferred that x and z are the same in a given antisense oligonucleotide. Accordingly, the following basic designs or structures of the antisense oligonucleotides of the third generation can be as follows: cap-$(n_p)_5(N_s)_7(n_p)_5$-cap, cap-$(n_p)_6(N_s)_7(n_p)_5$-cap, cap-$(n_p)_7(N_s)_7(n_p)_5$-cap, cap-$(n_p)_5(N_s)_8(n_p)_5$-cap, cap-$(n_p)_6(N_s)_8(n_p)_5$-cap, cap-$(n_p)_7(N_s)_8(n_p)_5$-cap, cap-$(n_p)_5(N_s)_9(n_p)_5$-cap, cap-$(n_p)_6(N_s)_9(n_p)_5$-cap, cap-$(n_p)_7(N_s)_9(n_p)_5$-cap, cap-$(n_p)_5(N_s)_7(n_p)_6$-cap, cap-$(n_p)_6(N_s)_7(n_p)_6$-cap, cap-$(n_p)_7(N_s)_7(n_p)_6$-cap, cap-$(n_p)_5(N_s)_8(n_p)_6$-cap, cap-$(n_p)_6(N_s)_8(n_p)_6$-cap, cap-$(n_p)_7(N_s)_8(n_p)_6$-cap, cap-$(n_p)_5(N_s)_9(n_p)_6$-cap, cap-$(n_p)_6(N_s)_9(n_p)_6$-cap, cap-$(n_p)_7(N_s)_9(n_p)_6$-cap, cap-$(n_p)_5(N_s)_7(n_p)_7$-cap, cap-$(n_p)_6(N_s)_7(n_p)_7$-cap, cap-$(n_p)_7(N_s)_7(n_p)_7$cap, cap-$(n_p)_5(N_s)_8(n_p)_7$-cap, cap-$(n_p)_6(N_s)_8(n_p)_7$-cap, cap-$(n_p)_7(N_s)_8(n_p)_7$-cap, cap-$(n_p)_5(N_s)_9(n_p)_7$-cap, cap-$(n_p)_6(N_s)_9(n_p)_7$-cap and cap-$(n_p)_7(N_s)_9(n_p)_7$-cap.

A further class of compounds which may be generated based on the technical teaching given herein and which may be used as medicaments and/or diagnostic agents are small interfering RNA (siRNA) directed to the nucleic acids, preferably mRNA, coding for the CD3 kappa peptides. siRNA is a double stranded RNA having typically a length of about 21 to about 23 nucleotides. The sequence of one of the two RNA strands corresponds to the sequence of the target nucleic acid such as the nucleic acid coding for the CD3 kappa peptides, to be degraded. Most specifically the siRNA is directed against the fusion region of CD3 kappa corresponding to the region encoded by exon 1, the part of exon 2 and exon 4 to prevent effects on the expression of CD3 delta. This kind of consideration is, in principle, applicable to all of the various classes of compounds of CD3 kappa related compounds as disclosed herein and thus defines a preferred specificity thereof. In other words, knowing the nucleic acid sequences of the target molecule, in the present case the CD3 kappa peptides, preferably the mRNA sequence, a double stranded RNA may be designed with one of the two strands being complementary to said, e.g. mRNA of the CD3 kappa peptides and, upon application of said siRNA to a system containing the gene, genomic DNA, hnRNA or mRNA coding for the CD3 kappa peptides, the respective target nucleic acid will be degraded and thus the level of the respective protein be reduced. The basic principles of designing, constructing and using said siRNA as medicament and diagnostic agent, respectively, is, among others, described in international patent applications WO 00/44895 and WO 01/75164.

Based on the aforementioned design principles, it is possible to generate such siRNA, antisense oligonucleotide and ribozyme, respectively, once the nucleic acid sequences coding for the CD3 kappa peptides are known. This is also true for precursor molecules of nucleic acid such as hnRNA, cDNA and the like, including genomic nucleic acid. Of course, also knowing the respective antisense strand may allow the design of such nucleic acid based compounds given the basic principle of base pair complementarity, preferably based on Watson-Crick base pairing. Accordingly, a further aspect of the present invention is related to specific siRNAs, ribozymes and antisense nucleotides which are directed against or specific for the CD3 kappa peptides. In the following, this is further illustrated by siRNA, however, this applies to antisense oligonucleotides and ribozymes as well, as will be acknowledged by the ones skilled in the art.

Such siRNA comprises preferably a length of from 15 to 25 nucleotides, whereby this means actually any length comprising 15, 16, 17, 18, 19, 20, 21, 22, 23, 24 or 25 nucleotides. In further embodiments, the siRNA may even exhibit more nucleotides. According the design principles well known in the art, respective siRNA can be generated. Accordingly, the siRNA claimed herein comprises a stretch of preferably any nucleotide length from 15 to 25 consecutive nucleotides which is either at least partially complementary to the sense or to the antisense strand encoding the CD3 kappa peptides, and a second ribonucleotide strand which is at least partially complementary to the first one and thus to the antisense strand and sense strand respectively, encoding the CD3 kappa peptides. Any design principle known in the art of generation or manufacture of siRNA may be applied to this kind of duplex structure. The siRNA space disclosed herein comprises siRNA molecules whereby the antisense strand of which starts with a nucleotide which corresponds to nucleotide no. 1 of a sequence coding for the CD3 kappa peptides as specified above. Further such siRNA molecules start with a nucleotide which corresponds to the nucleotide no 2 of a sequence coding for the CD3 kappa peptides as specified above, and so on. This kind of scanning over the sequence coding for the CD3 kappa peptides is repeated so as to provide all possible siRNA molecules which can be directed against the CD3 kappa peptides. The length of any of the siRNA molecules thus generated may be any length suitable for siRNA, more particularly any length as specified above. Preferably, the various siRNA molecule of the siRNA molecule space disclosed herein, overlap except the most 5' terminal nucleotide of the antisense strand or sense strand. It is obvious that the thus obtained antisense sequences have to complement through base pairing so as to form the at least partially double-stranded structure required for a functionally active siRNA Based on the mode of action of the aforementioned classes of compounds, such as antibodies, peptides, anticalines, aptamers, spiegelmers, ribozymes, antisense oligonucleotides as well as siRNA, it is thus also within the present invention to use any of these compounds targeting the CD3 kappa peptides and the nucleic acid coding therefor, respectively, for the manufacture of a medicament or a diagnostic agent for any of the diseases as described herein and any of the diseased conditions described herein. Furthermore, these agents may be used to monitor the progression of said diseases and diseased conditions and the success of any therapy applied, respectively.

The various classes of compounds designed according to the present invention such as antibodies, peptides, anticalines, small molecules, aptamers, spiegelmers, ribozymes, antisense oligonucleotides and siRNA may also be contained in a pharmaceutical composition. Preferably such pharmaceutical composition is used for the treatment of the diseases as described herein or the diseased conditions described herein. The pharmaceutical composition may comprise in an embodiment one or several of the aforementioned classes of compounds and/or one or more members of a single class, and optionally a further pharmaceutical active compound, and a pharmaceutically acceptable carrier. Such carrier may be either liquid or solid, for example a solution, a buffer, an alcoholic solution or the like. Suitable solid carriers are, among others, starch and the like. It is known to the one skilled in the art to provide respective formulations for the various compounds according to the aforementioned classes of compounds in order to realize the particular route of administrations such as oral, parenteral, subcutaneous, intravenous, intramuscular and the like.

The various compounds of the different classes of compounds as mentioned above, may also be, either alone or in combination, subject to or contained in a kit. Such kit comprises apart from the respective compound(s) additionally one or several further elements or compounds whereby the elements are selected from the group comprising buffers, negative controls, positive controls and instructions on the use of the various compounds. Preferably, the various compounds are present in either dry or liquid form, preferably as a unit dosage for a single administration each. The kit may particularly be used for the therapy, diagnosis or monitoring of the progress of the disease or applied therapies in relation to the diseases and diseased conditions as described herein.

EXAMPLE 1

Materials and Methods

Peptide Synthesis

The purity and identity of the peptides (WITA, Teltow, Germany) was checked by reverse-phase HPLC and matrix-assisted laser desorption ionization mass spectroscopy. The 42 amino acid long CD3kappa (SQVSPFKIPIEELEDRVFVNCNTSIYRASSLSN CRHTSSVEE) (SEQ ID NO:4) had a purity of >99,9999%, while the control peptide (SESVNISTNVNRFHTFPYCEIAEVSCRSKVRIELDLQSPESS) (SEQ ID NO:4438) with the same amino acid composition but a random sequence had a purity of >98%.

Origin of Human Materials

All materials were taken from patients after informed consent. Peripheral blood mononuclear cells (PBMCs) were obtained from normal individuals (laboratory personnel). Splenocytes were isolated from spleens removed from cadaveric organ donors provided for HLA-typing and crossmatch studies in the context of liver transplantation.

Joint effusion fluids from rheumatoid arthritis patients were obtained in the context of therapeutic joint puncture.

Preparation of PBMCs

Heparinized full blood was layered on room-temperature LSM (density: 1.077 g/ml, Cambrex, Verviers, Belgium). After centrifugation at 400 g at 20° C. for 30 minutes, the interphase cells were isolated. The cells were washed twice with 50 ml PBS containing 2 mM EDTA and centrifuged at 300 g for 10 minutes at 20° C. The cell-pellet was resuspended in RPMI supplemented with 10% autologous serum, Pen/Strep, Gentamycin, Pyruvate, Hepes-buffer and L-Glutamine (Cambrex).

T Cell Cultures

PBMCs were used from Donor 1 (DRB1*0401, 1501), Donor 2 (DRB1*1501, DRB1*1601, DQB1*0502, DQB1*0602) and Donor 3 (DRB1*0701, DRB1*1501, DQB1*0303, DQB1*0602). PBMCs were incubated with 10 μM peptide and 100 U/ml IL-2 at $5\times10^6$ cells/ml for 30-40 days. 20 U/ml IL-2 was added every 4 days. The cultures were restimulated four times before analysis with the same conditions.

Generation of Dendritic Cells and T-Cell Stimulation

The in vitro priming with Dendritic cells (DC) was performed with peptide labeled DCs generated from peripheral blood monocytes. The adherent monocytes were treated with 1000 U/ml GM-CSF (BD) and 1000 U/ml IL-4 (BD) for 8 days. Non-adherent mature DCs were activated by addition of 1000 U/ml TNFα (BD), 50 ng/ml IL-1 (BD) and 1 μM Prostaglandin E2 (Calbiochem, Schwalbach, Germany). The peptide labeled DCs (labeled with 100 μM peptide for 2 h) were mixed in a ratio of 1:50 with fresh isolated PBMCs and 100 U/ml IL-2, 50 ng/ml IL-7 (BD) and 50 ng/ml IL-15 (BD) were added. The further culture and restimulation was performed as describe above.

CD3 Delta RT-PCR

All reagents were from Qiagen (Hilden, Germany) if not otherwise stated. $10^7$ cells were stimulated and centrifuged as in the Cytokine capture assay. The pellet was resuspended in 600 μl Buffer RLT. Samples were homogenized with QIAshredder columns and 1 volume of 70% ethanol was added. RNA was bound to RNeasy mini spin column by centrifugation for 15 sec at 8000 g, followed by one wash step with 700 μl Buffer RW1 and two wash steps with 500 μA Buffer RPE. RNA was eluted in 650 μl water, mixed with 650 μl buffer OBB and 30 μl Oligotex suspension. The samples were incubated for 3 minute at 70° C. and placed at room temperature for 10 minutes. The Oligotex:mRNA complex was pelleted by centrifugation for 2 min at 18000 g and resuspended in 600 μl Buffer OW2. The suspension was pipetted onto a spin column and washed with 600 μl Buffer OW2. mRNA was eluted with 20 μl 70° C. Buffer OEB. cDNA-synthesis was performed for 2 h at 50° C. with the following reaction mix: 2 μl 10×RT Buffer, 2 μl dNTP Mix (5 mM of each dNTP), 0.4 μl Oligo-dT primer (50 μM, Perkin Elmer), 0.5 μl Sensicript, 0.5 μl Omniscript and 14.6 μl mRNA. PCR included 12.5 μl HotStarTaq Mastermix, 0.25 μl huCD3d-5 (50 μM, TTCAAGATACCTATAGAGGAACTTGAGGAC) (SEQ ID NO:4439), 0.25 μl huCD3d-3 (50 μM, TAGACCTGGTCATTCCTCAACAGAGCTTG) (SEQ ID NO:4440) and 12 μl cDNA. The PCR conditions were 40 cycles of 45 sec at 96° C., 45 sec at 64° C. and 60 sec at 72° C. The PCR product was separated on a 1% agarose gel and the 220 bp band excised. The DNA was isolated with QIAEX and ligated in the PCR 2.1 vector (Invitrogene, Karlsruhe, Germany). TOP10 *E. coli* (Invitrogene) were transformed with the ligation product and plated with 100 μg/ml ampicillin. Plasmid minipreps of four individual clones were sequenced each two times with the PCR primers. 100% identical sequences were obtained from all eight sequencing results.

Functional CD3 Kappa Assays

CD3 kappa or the control peptide was solubilized in RPMI with 1% human serum albumin (HSA, Calbiochem, Schwalbach, Germany) and 100 μM β-mercaptoethanol (β-ME, Invitrogene) at 10 mg/ml. PBMCs were incubated at $10^6$ cells/ml with either peptide in the same medium and stained after on wash step with PBS with various antibodies (BD).

Protein Microarrays

All reagents were from Raybiotech (Hilden, Germany). 2 ml supernatant from cultures with $5\times10^6$ cells/ml was mixed with blocking buffer (BB) and pipetted to blocked human cytokine micro arrays 6.1 and 7.1. After overnight incubation, the membranes were washed three times with wash buffer I and two times with wash buffer II. Anti-cytokine antibodies were added in 2 ml BB. After incubation and wash as described above, 2 ml streptavidin-HRP was added. Again after incubation and wash as described above, detection solution was added and exposure for 18 h to X-ray films were performed.

EXAMPLE 2

Identification of CD3 Kappa

CD 3 kappa was found in T-cell cultures upon stimulation with heteroclitic peptides resulting in an increased expression of IFN-gamma, CD4 and TCR. CD3 kappa is a splice variant of CD3 delta and was not present in T-cells which were challenged with the same heteroclitic peptide but did not increase IFN gamma production. Also, normal human splenocytes used as control showed the expected full length CD3-delta-cDNA, but not CD3 kappa and the corresponding 220 bp fragment as may be taken from FIG. 1A.

The inventors also found CD3 kappa expression in peripheral blood mononuclear cells (PBMCs) from healthy donors and from patients with different autoimmune diseases. Surprisingly two of three samples from knee effusions of patients with rheumatoid arthritis showed only the expression of this 220 bp band and no full length CD3delta expression as may be taken from FIG. 1B. In vitro primed T cells, stimulated with dendritic cells, IL-2, IL-7, IL-15 and loaded with cross-reactive peptides derived from a human tumor-associated antigen expressed this 220 bp band, while it was lacking in the same cultures in the absence of in vitro priming (see FIG. 1A and FIG. 1C). The 220 bp variant was sequenced and identified as a novel splice variant of CD3-delta, which is missing exon 3 and a part of exon 2 but contains the complete exons 1, 4 and 5 as depicted in FIG. 1D. This alternative splicing results in a frame shift in exon 2 and yields an open reading frame of 174 bp. The resulting polypeptide has still the first 41 N-terminal amino acids of CD3delta, including the signal peptide. However the C-terminus has a completely different sequence, whereby a transmembrane region is missing which is deemed the reason that the polypeptide is secreted. The putative CD3kappa peptide as produced by the ribosome should thus contain 58 amino acids, including the 17 new amino acids encoded by the overlap region of exon 2 and exon 3 (SEQ ID NO:1). However, the hydrophobic signal peptide is removed during transfer in the endoplasmic reticulum and therefore the secreted CD3kappa should not contain the first 16 amino acids. We synthesized the resulting 42 amino acids polypeptide without the signal peptide.

EXAMPLE 3

Effect of CD3 Kappa on TCR Expression

Figure 2A:
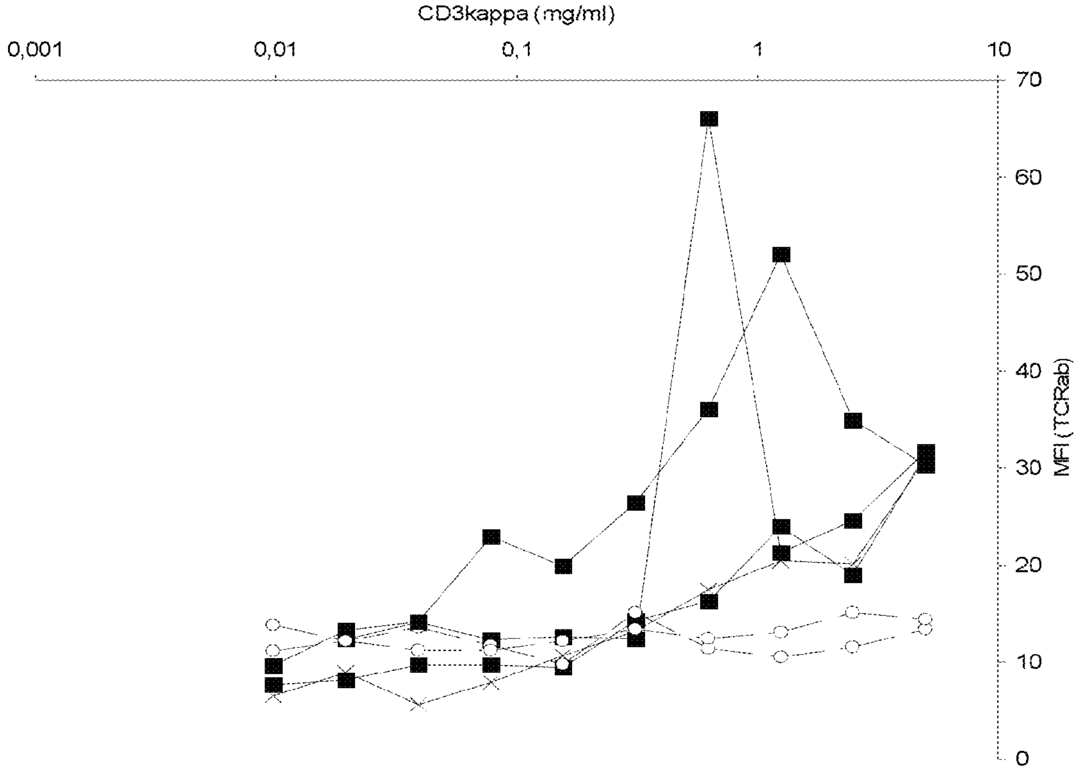
FIG. 2*a* is a histogram indicating the surface expression strength of CD4+ PBMCs expressing TCR upon treatment with CD3 kappa (■) or with a control peptide (o: same amino-acid composition, but random sequence); whereby also one sample of CD4+ PBMCs expressing TCR upon treatment with CD3 kappa together with PMA and ionomycin is also shown (x)

We synthesized the resulting 42 amino acids polypeptide without the signal sequence resulting in the CD3 kappa peptide having the amino acid sequence according to SEQ ID NO:4. All following experiments were performed with freshly isolated PBMCs from healthy donors in the presence of the 42-mer CD3-kappa or of a control peptide (consisting of the same amino acid composition and length but with a random sequence). The CD4+ cells from three healthy donors showed a concentration dependent increase in TCR-expression after 24 h as may be taken from FIG. 2A, with a detectable TCR-upregulation after treatment with 0.1 mg/ml CD3-kappa or more. Stimulation of the cells with PMA and ionomycin did not affect this finding. The control peptide had no effect on TCR expression. Concentrations up to 1 mg/ml CD3-kappa induced a maximal response after 24 h resulting in a six fold upregulation of the TCR.

Figure 2B:
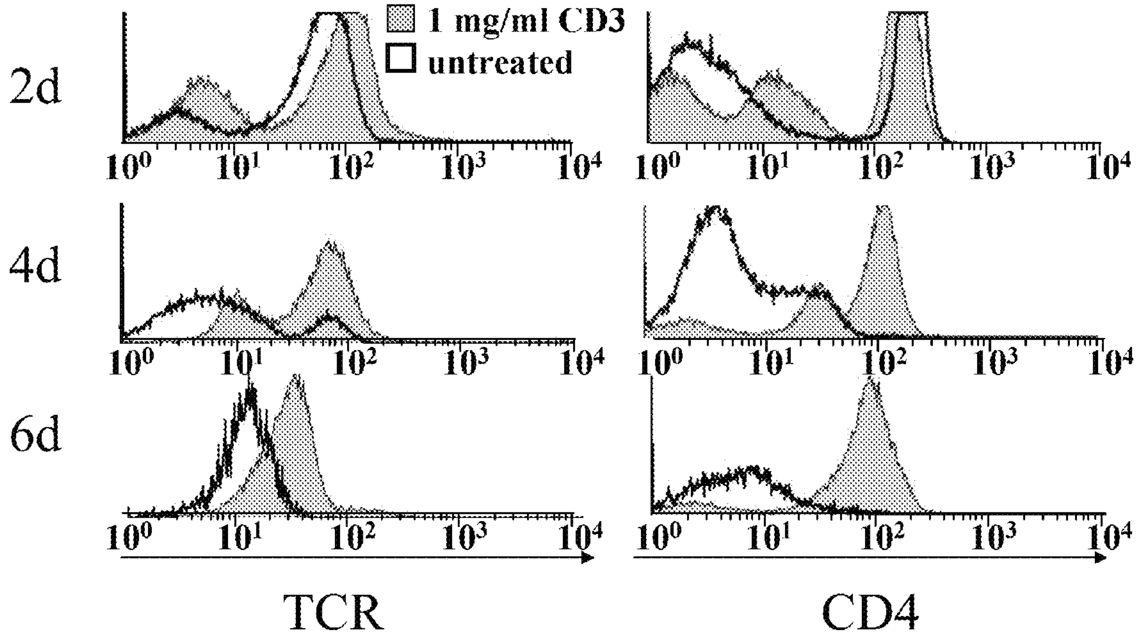
FIG. 2*b* shows histograms indicating the surface expression strength of CD4+ PBMCs expressing TCR and CD4 upon treatment with CD3 kappa, whereby a kinetic ranging from two to six days is shown.

Addition of CD3-kappa to PBMCs lead to a remarkable and sustained increase of TCR and CD4 expression over the next 6 days as may be taken from FIG. 2B. The TCR-expression level was stabilized after treatment with CD3-kappa in a majority of the CD4 cells, while untreated cells quickly converted to a low TCR expression state. Only at day 6 did the CD3-kappa treated cells show a decline in TCR expression. The CD4-expression was nearly completely stable over 6d after treatment with CD3-kappa while it was dramatically down regulated after 48 h in the control cultures.

EXAMPLE 4

Impact of CD3 Kappa on Cellsurface Markers

Figure 3A:
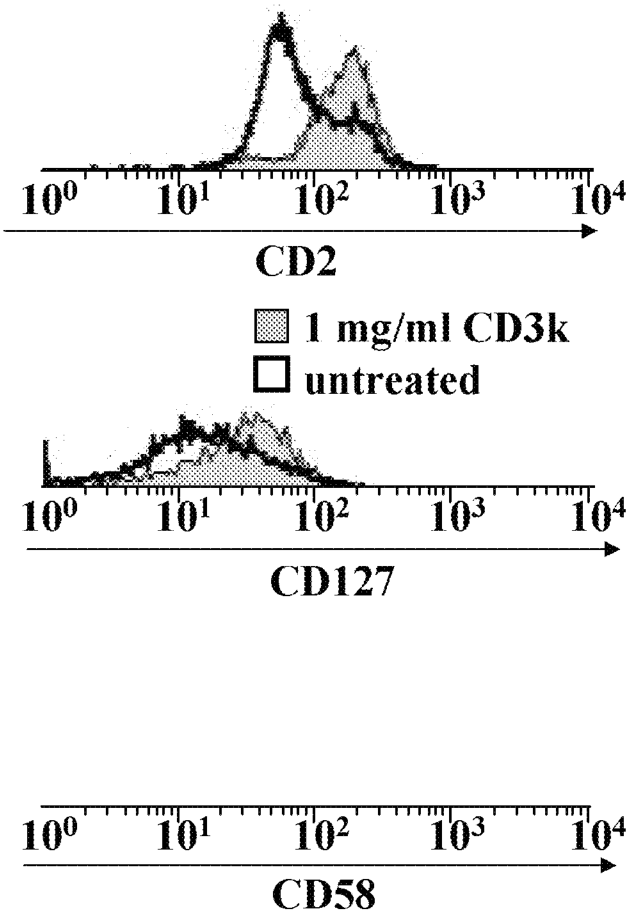
FIG. 3*a* is a histogram indicating the surface expression strength of PBMCs expressing surface markers CD2, CD127 and CD58 upon treatment and non-treatment with CD3 kappa after six days.
Figure 4A:
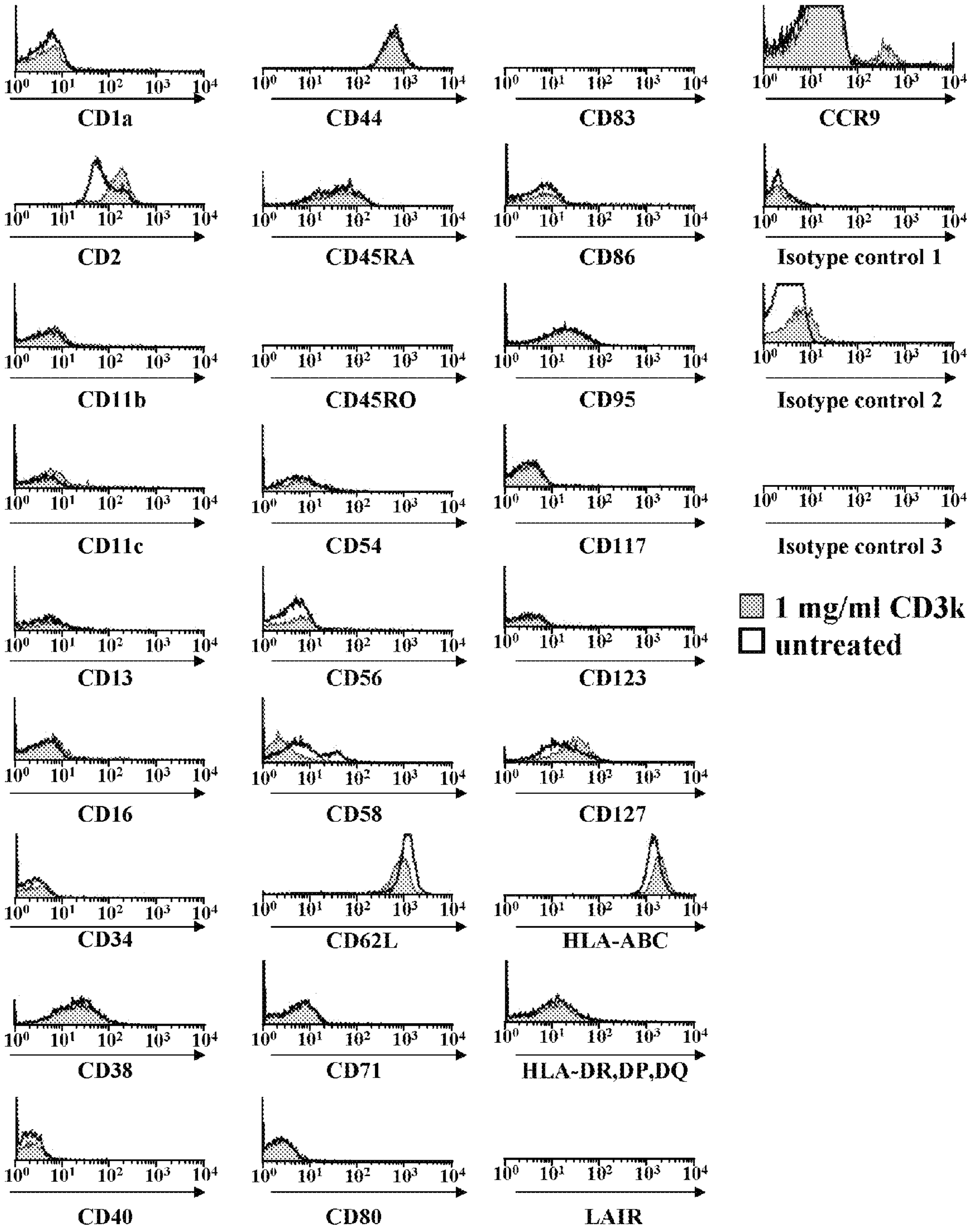
FIG. 4*a* depicts histograms indicating the surface expression strength of PBMCs expressing various surface markers upon treatment and non-treatment with CD3 kappa after six days.
Figure 4B:
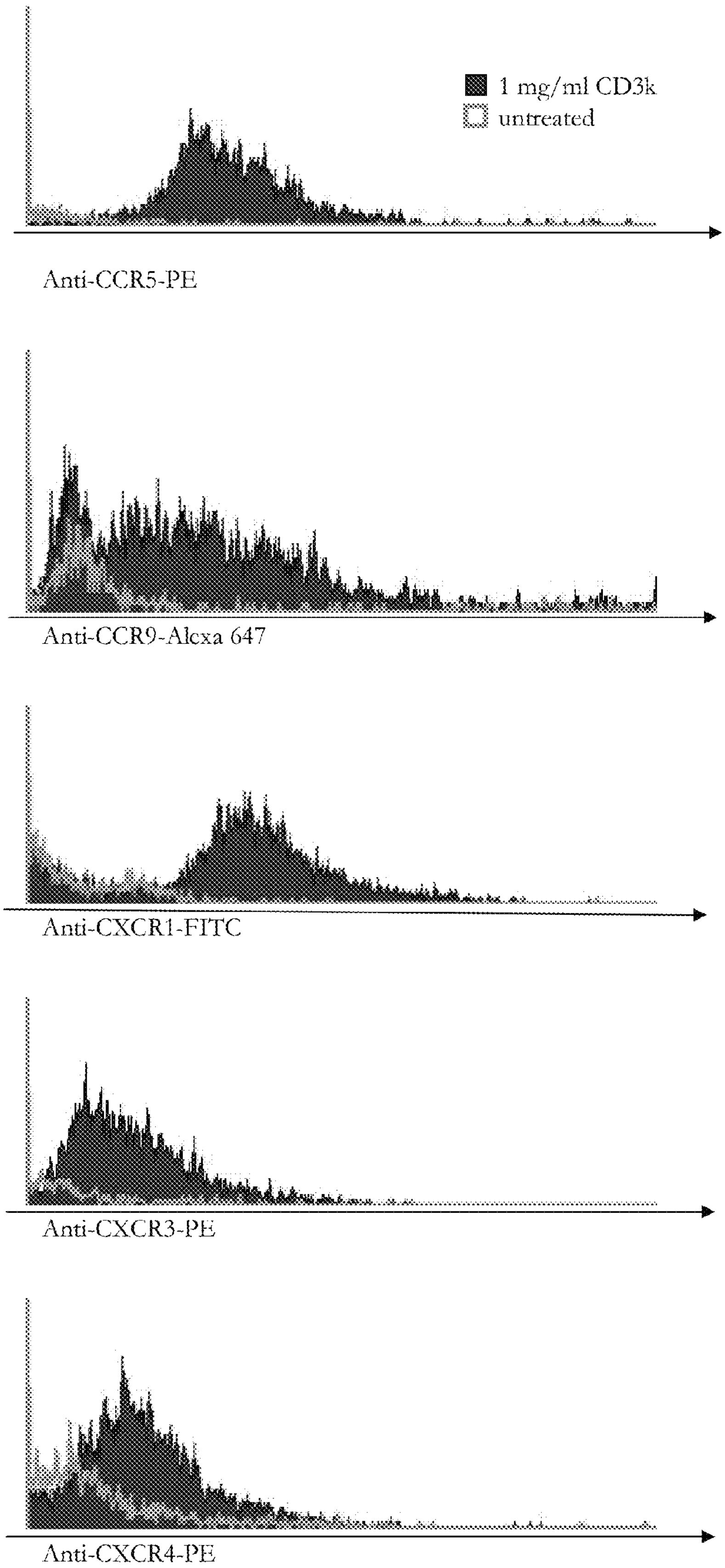
FIG. 4*b* depicts histograms indicating the surface expression strength of PBMCs expressing cytokine- or chemokine-receptors upon treatment and non-treatment with CD3 kappa after six days.
Figure 4B:
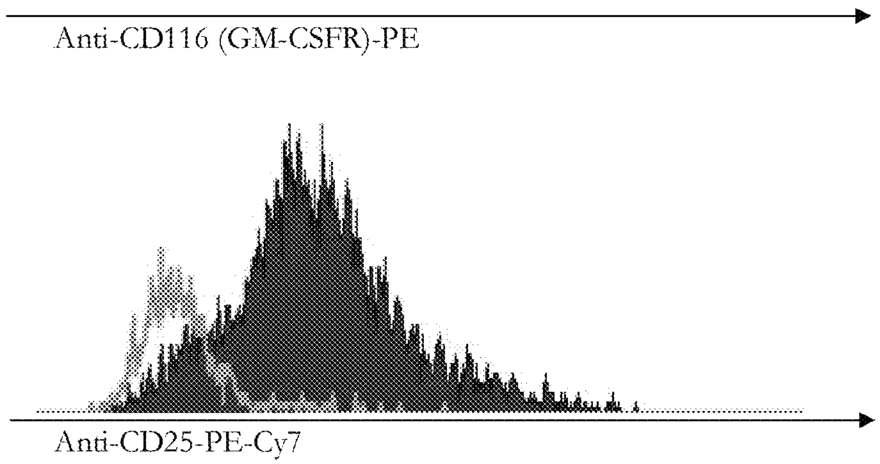

Analysis of the cell surface markers after addition of CD3-kappa showed an increase in the expression of CD2, CD25, CD116, CD127, CCR3, CCR9 and CXCR1. CD3kappa also leads to an a slight upregulation of CXCR3 and CXCR4 as may be taken from FIGS. 3*a*, 4*a* and 4*b*.

Figure 3B:
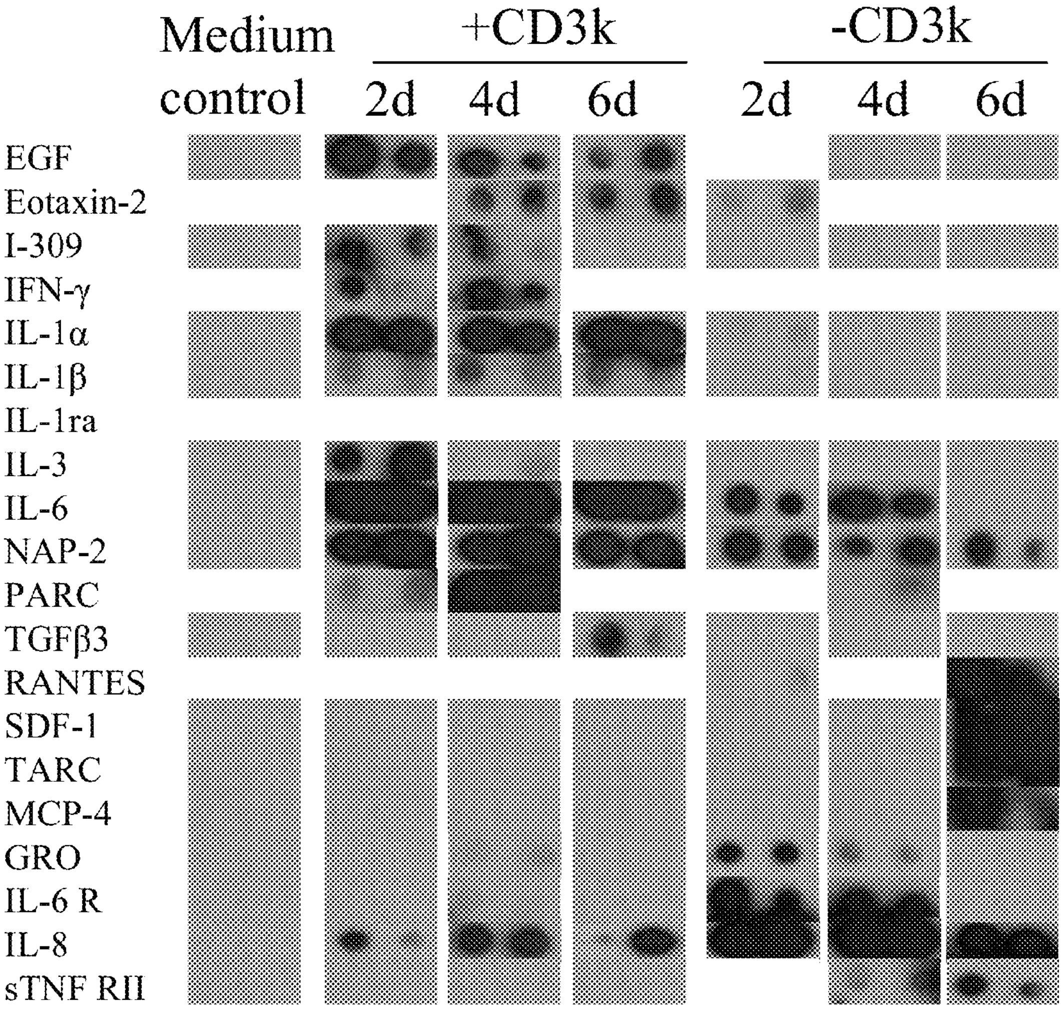
FIG. 3*b* is a Western Blot of a dot blot microarray analysis of T cell secreted factors after various time points, whereby only significant changes cytokine expressions and double dot blots are shown.
Figure 3C:
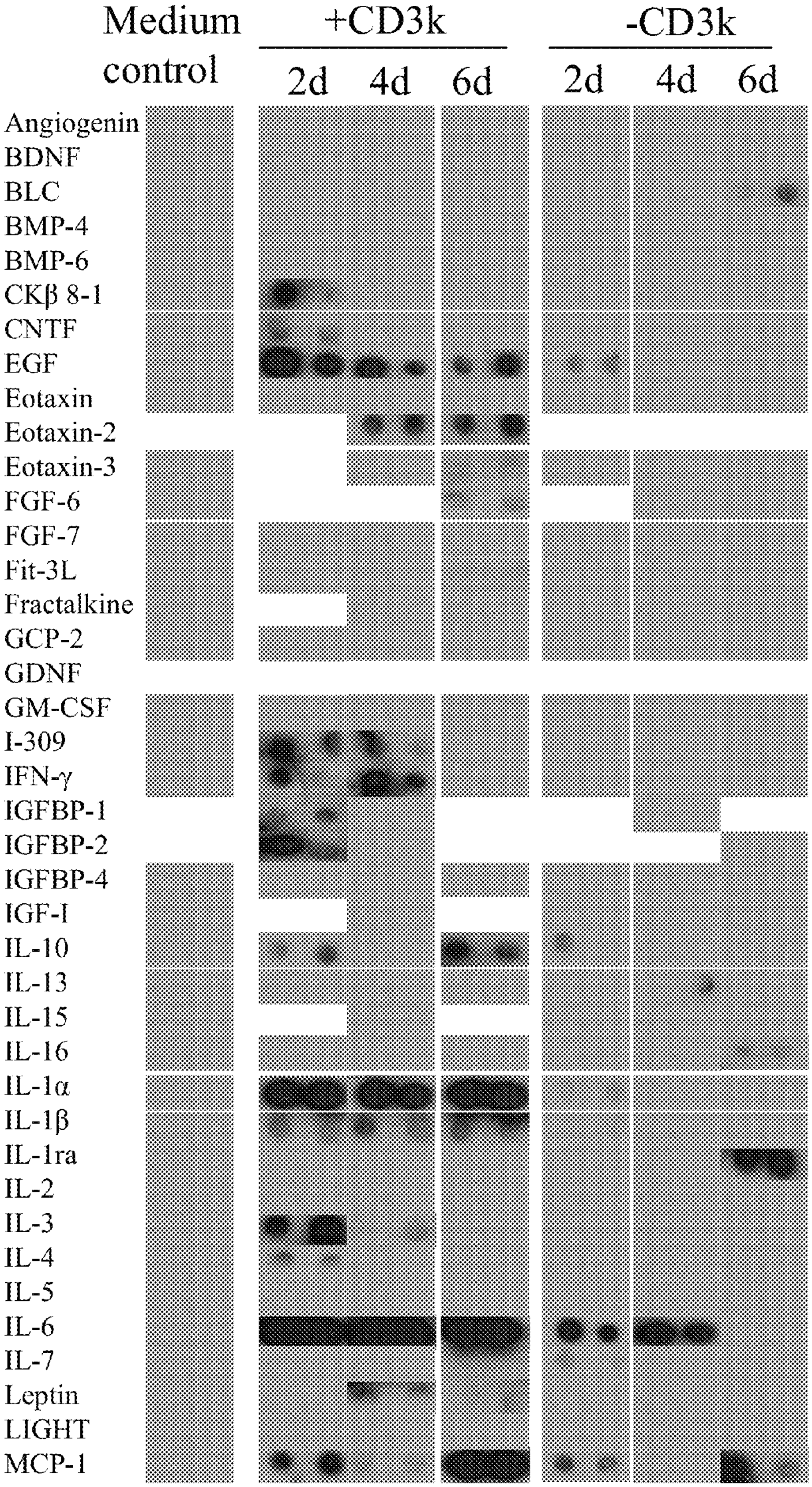
FIG. 3*c* is a Western Blot of a dot blot microarray analysis of T cell secreted factors after various time points, whereby all analyzed cytokine expression patterns and double dot blots are shown.
Figure 3C:
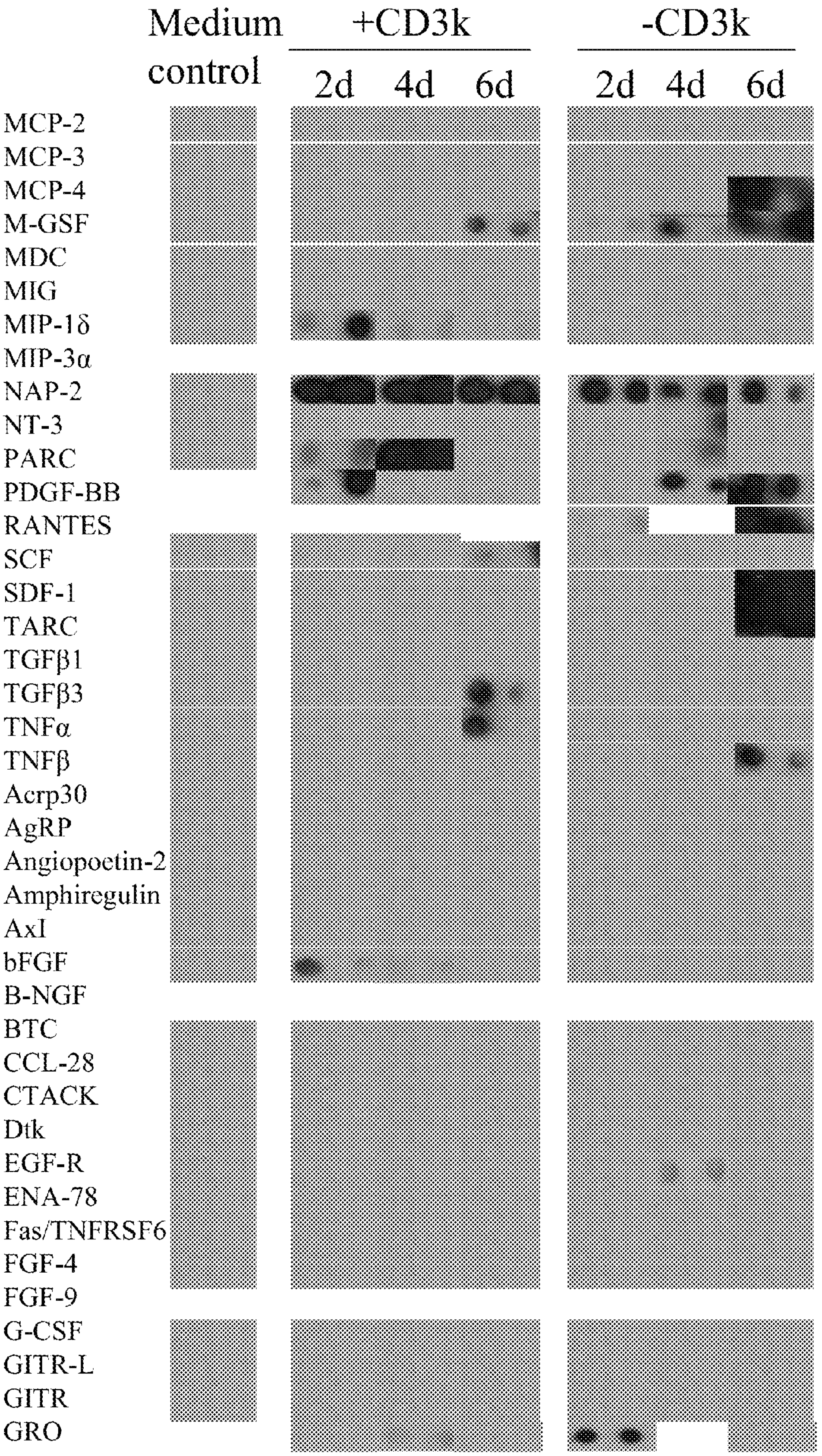
Figure 3C:
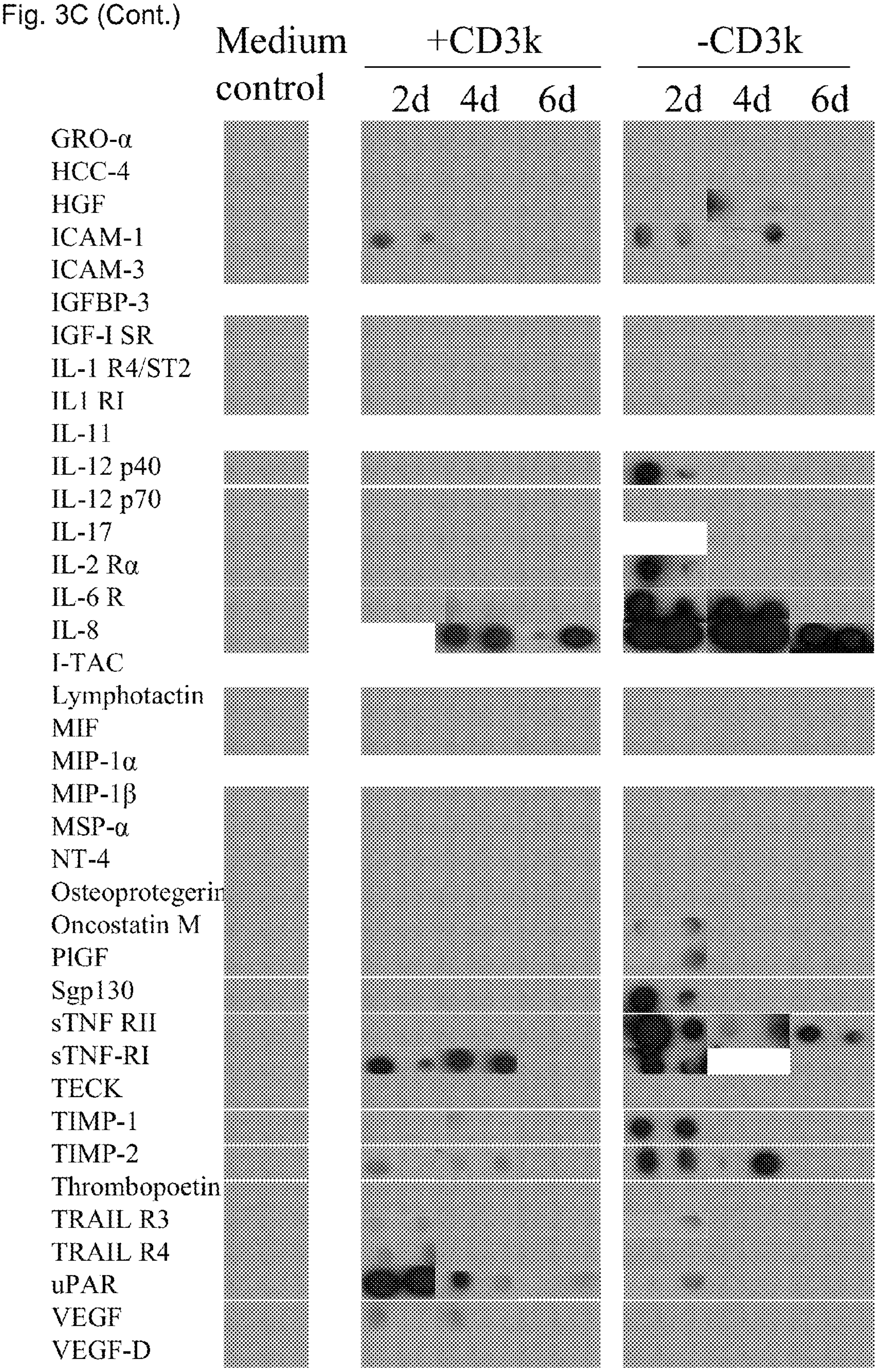

CD58 was down regulated. The expression of CD38, CD44, CD45RA, CD45RO, CD62L, CD95, HLA-ABC, HLA-DR, DP, DQ and LAIR was not changed and non-T-cell markers were not affected as may be taken from FIG. 4*a*. The amount of EGF, Eotaxin-2, I-309, IFNγ, IL-1α, IL-1β, IL-3, IL-6, NAP-2, TGFβ3 and PARC in the supernatant was increased after CD3-kappa treatment, while the amount of IL-1ra, IL-8, RANTES, SDF-1, TARC, MCP-4, GRO, soluble IL-6 Receptor and soluble TNF-Receptor II was decreased as may be taken from FIGS. 3*b* and 3*c*.

EXAMPLE 5

Figure 5:
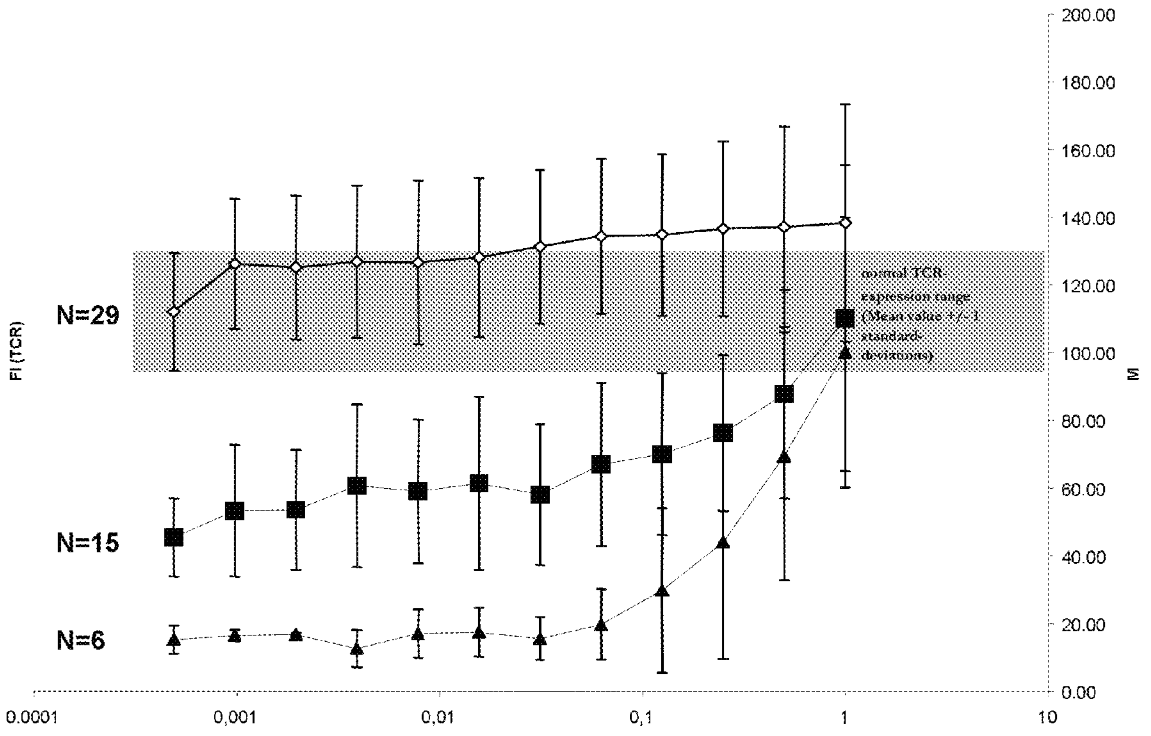
FIG. 5 is a histogram indicating the surface expression strength of CD4+ PBMCs form healthy controls and patients expressing TCR upon treatment with CD3 kappa, whereby 29 donors with normal expression range (o), 15 donors with a significantly reduced TCR-expression (■) and 6 donors with a even more significantly reduced TCR-expression due to high doses of cytostatic chemotherapy (▲) are shown.

Effect of CD3 Kappa on PBMCs from Patients Recovering from T-Cell Toxic Chemotherapy While CD3 kappa lead to a six-fold TCR upregulation in PBMCs from healthy donors, the analysis of CD3 kappa-associated TCR expression in PBMCs from patients recovering from treatment with the T-cell toxic chemotherapeutic agent fludarabine showed a dramatic decreased TCR expression which could be restored to normal levels by means of a 25-fold TCR upregulation after 48 h treatment with CD3 kappa as depicted in FIG. 5. CD3 zeta is synthesized at about 10% of the rate as the other CD3-complex proteins being the limiting component for a correct assembly of the CD3/TCR complex. A maximal upregulation of CD3 zeta can therefore result in a 10-fold upregulation of the TCR. The higher capability of CD3 kappa to upregulate the surface TCR expression might be explained with a reduced need of some of the CD3-complex components.

For the first time, we thus describe herein a molecular mechanism which may explain the increased avidity of cross-reactive T cells induced by heteroclitic peptide vaccination and possibly by molecular mimicry during autoimmune diseases. Our immune system is continuously being challenged by a myriad of pathogens, and there is a high likelihood that some of these antigens differ only slightly from self antigens. The detection of CD3kappa expressing cells in peripheral blood of normal individuals reflects such a situation with a small number of cross-reactive T cells with upregulated CD3kappa, while the predominance of CD3kappa bearing lymphocytes in the joint of arthritis patients reflects the expansion of a cross-reactive T-cell population. The demonstration of CD3kappa in peripheral blood lymphocytes stimulated with Dendritic cells might be due to the expansion of low affinity cross-reactive T cells, which cannot be supported in the absence of Dendritic cells. Moreover our findings support the use of CD3kappa and the derivatives described herein, including the nucleic acids coding therefore, as an adjuvant in vaccination against poorly immunogenic antigens.

The features of the present invention disclosed in the specification, the claims and/or the drawings may both separately and in any combination thereof be material for realizing the invention in various forms thereof.

SEQUENCE LISTING

The patent contains a lengthy “Sequence Listing” section. A copy of the “Sequence Listing” is available in electronic form from the USPTO web site (http://seqdata.uspto.gov/?pageRequest=docDetail&DocID=US09085641B2). An electronic copy of the “Sequence Listing” will also be available from the USPTO upon request and payment of the fee set forth in 37 CFR 1.19(b)(3).

What is claimed is:

1. A synthetic peptide comprising the amino acid sequence of SEQ ID NO:4, the peptide blocks or reduces internalization of the T cell receptor.

2. A synthetic peptide consisting of the amino acid sequence of SEQ ID NO:1.

3. The synthetic peptide according to claim 1, wherein the peptide does not encode exon 3 of CD3 gene complex.

4. The synthetic peptide according to claim 1, wherein peptide is the amino acid sequence of SEQ ID NO:4.

5. A composition comprising the synthetic peptide according to the amino acid sequence of SEQ ID NO:4; and a pharmaceutically acceptable carrier, wherein the peptide blocks or reduces internalization of the T cell receptor.

* * * * *